US007417059B2

(12) United States Patent
Tamura et al.

(10) Patent No.: US 7,417,059 B2
(45) Date of Patent: *Aug. 26, 2008

(54) SUBSTITUTED AROMATIC-RING COMPOUNDS, PROCESS FOR PRODUCING THE SAME AND USE

(75) Inventors: Norikazu Tamura, Kobe (JP); Takashi Ichikawa, Suita (JP); Masayuki Ii, Minoo (JP)

(73) Assignee: Takeda Pharmacetical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/094,210

(22) Filed: Mar. 31, 2005

(65) Prior Publication Data

US 2005/0176783 A1 Aug. 11, 2005

Related U.S. Application Data

(62) Division of application No. 10/048,938, filed as application No. PCT/JP00/05197 on Aug. 3, 2000, now Pat. No. 7,078,540.

(30) Foreign Application Priority Data

Aug. 6, 1999 (JP) ................. 11-224248

(51) Int. Cl.
```
A61K 31/44    (2006.01)
A61K 31/38    (2006.01)
A61K 31/35    (2006.01)
A61K 31/235   (2006.01)
A61K 31/34    (2006.01)
A61K 31/18    (2006.01)
C07D 211/00   (2006.01)
C07D 211/08   (2006.01)
C07D 335/02   (2006.01)
C07D 309/00   (2006.01)
C07D 315/00   (2006.01)
C07C 321/00   (2006.01)
C07C 303/00   (2006.01)
C07C 315/00   (2006.01)
```
(52) U.S. Cl. .............. 514/350; 514/351; 514/354; 514/357; 514/432; 514/459; 514/460; 514/532; 514/538; 514/603; 546/184; 546/192; 549/28; 549/356; 549/416; 549/426; 549/427; 549/428; 560/9; 560/12; 560/13; 564/80; 568/28; 568/30; 568/31; 568/36

(58) Field of Classification Search ........... 514/602, 514/359, 383, 520, 521, 522, 530, 538, 562, 514/601, 603, 604, 373; 548/166, 250, 252, 548/255, 269.4, 418; 560/12, 13; 562/430; 564/91, 92; 549/356, 429

See application file for complete search history.

(56) References Cited

U.S. PATENT DOCUMENTS

| 5,378,703 | A   | 1/1995  | Dean et al. |
| 6,495,604 | B1  | 12/2002 | Ichimori et al. |
| 7,078,540 | B1* | 7/2006  | Tamura et al. ............. 549/420 |
| 2003/0100580 | A1 | 5/2003 | Dhanak et al. |
| 2004/0002425 | A1 | 1/2004 | Saitou et al. |

FOREIGN PATENT DOCUMENTS

| WO | 96/31492 | 10/1996 |
| WO | 99/46242 | 9/1999 |

OTHER PUBLICATIONS

Försterman et al., "Nitric Oxide Synthase Isozymes—Characterization, Purification, Molecular Cloning, and Functions," Hypertension, 23(No. 6, pt. 2), 1121-1131 (Jun. 1994).*
Kröncke et al., "Inducible Nitric Oxide Synthase in Human Diseases," Clinical and Expimental Immunology, 113, 147-156 (1998).*
Yamada et al., "Discovery of Novel and Potent Small-Molecule Inhibitors of NO and Cytokine Production as Antisepsis Agents: Synthesis and Biological Activity and Alkyl 6-(N-Substituted sulfamyl)cyclohexy-1-ene-1-carboxylate," J. Medicinal Chemistry, 48(23), 7457-7467 (2005); WEB publ Oct. 14, 2005.*
Pugh et al. (eds.), Stedman's Medical Dictionary, 27th Edition, Lippincott Williams & Wilkins, Baltimore, MD, 2000, only p. 1021 supplied.*
Ketteler et al., "Nitric Oxide in Sepsis-Syndrome: Potential Treatment of Septic Skock by Nitric Oxide Synthase Antagonists," Kidney International, 53(Suppl. 64), S27-S30 (1998): copy supplied by applicant.*
Satoh et al., "Induicble Nitric Oxide Synthase and Tumor Necrosis Factor-Alpha in Myocardium in Human Dilated Cardiomyopathy," Journal of the American College of Cardiology, 29(4), 716-724 (Mar. 15, 1997): copy supplied by applicant.*
Ishiyama et al., "Nitric Oxide Contributes to the Progression of Myocardial Damage in Experimental Autoiummune Myocarditis in Rats," Circulation, 95(2), 489-496 (Jan. 21, 1997): copy supplied by applicant.*

(Continued)

Primary Examiner—L. E. Crane
(74) Attorney, Agent, or Firm—Wenderoth, Lind & Ponack, L.L.P.

(57) ABSTRACT

The present invention is directed to a class of cyclohexene derivatives bearing sulfamoyl and ester groups which have an inhibitory activity on nitric oxide (NO) production and cytokine production, and are useful as an agent for the prophylaxis and/or treatment of diseases such as, cardiac disease, autoimmune disease, inflammatory disease, central nervous system disease, infectious disease, sepsis, and septic shock.

14 Claims, No Drawings

OTHER PUBLICATIONS

Kettelhut et al., "The Toxic Effects of Tumor Necrosis Factor in vivo and Their Prevention by Cyclooxygenase Inhibitors," Proc. of the National Academy of Sciences USA, 84, 4273-4277 (Jun. 1987): copy supplied by applicant.*

Weisensee et al., "Effects of Cytokines on the Contractility of Cultured Cardiac Myocytes," International Journal of Immunopharmacology, 15(5), 581-5878 (1993): copy supplied by applicant.*

Robaye et al., "Tumor Necrosis Factor Induces Apoptosis (Programmedc Cell Death) in Normal Endothelial Cells in Vitro," American Journal of Pathology, 138(2), 447-453 (Feb. 1991): copy supplied by applicant.*

Graafland, T., et al. "Structure and reactivity in intramolecular catalysis. Catalysis of sulfonamide hydrolysis by the neighboring carboxyl group", J. Am. Chem. Soc., vol. 101, No. 23 (Nov. 7, 1979), pp. 6981-6991.

Teun Graafland, Wim C. Nieuwpoort and Jan B. F. N. Engberts, "Steric Effects in the Intramolecular Carboxyl-Catalyzed Hydrolysis of Sulfonamides. Ab Initio Quantum Chemical Studies of the Pentacoordinated Sulfur Intermediate" in *Journal of the American Chemical Society*, 1981, 103, pp. 4490-4494.

Katrin Illgen, Christine Hartung, Rainer Herzschuh and Bärbel Schulze, "3-Hydroperoxy-4,5,6,7-tetrahydro-toluene-2,a-sultims: Preparation and Reactions" in *Molecules*, presented Sep. 1-4, 1996, 1, pp. 139-141.

Bärbel Schulze, Sabine Kirrbach, Katrin Illgen and Peter Fuhrmann, "Synthesis of Stable Hydroperoxides of Sultams by Oxidation of Isothiazolium Salts" in *Tetrahedron*, Jan. 15, 1996, vol. 52, No. 3, pp. 783-790.

Arend et al., "IL-1 Receptor Antagonist and IL-1β Production in Human Monocytes are Regulated Differently", Journal of Immunology, vol. 147, No. 2, pp. 1530-1536, Sep. 1, 1991.

Dinarello et al., "Blocking IL-1: Interleukin 1 Receptor Antagonist in vivo and in vitro", Immunology Today, vol. 12, No. 11, pp. 404-410, 1991.

Neuner et al., "Pentoxifylline in vivo Down-Regulates the Release of IL-1β, IL-6, IL-8 and Tumor Necrosis Factor-α by Human Peripheral Blood Mononuclear Cells", Immunology, vol. 83, No. 2, pp. 262-267, Oct. 1994.

Matsuda et al., "Establishiment of an Interleukin 6 (IL6)/B Cell Stimulatory Factor 2-Dependent Cell Line and Preparation of Anti-IL6 Monoclonal Antibodies", European Journal of Immunology, vol. 18, pp. 951-956, Jun. 1988.

Cohen et al., "CNI-1493 Inhibits Monocyte/Macrophage Tumor Necrosis Factor by Suppression of Translation Efficiency", Proc. National Academy of Science USA, vol. 93, pp. 3967-3971, Apr. 1996.

Forstermann et al., "Nitric Oxide Synthase Isozymes—Characterization, Purification, Molecular Cloning, and Functions", Hypertension, vol. 23, No. 6, Part 2, pp. 1121-1131, Jun. 1994.

Kroncke et al., "Inducible Nitric Oxide Synthase in Human Diseases", Clinical and Experimental Immunology, vol. 113, pp. 147-156, 1998.

* cited by examiner

US 7,417,059 B2

SUBSTITUTED AROMATIC-RING COMPOUNDS, PROCESS FOR PRODUCING THE SAME AND USE

This is a divisional of Ser. No. 10/048,938, filed Feb. 6, 2002 now U.S. Pat. No. 7,078,540, which is a U.S. national stage of International Application No. PCT/JP00/05197 filed Aug. 3, 2000.

TECHNICAL FIELD

The present invention relates to a novel cycloalkene derivative having a suppressive activity on the production of inducible nitric oxide synthase-derived nitric oxide (NO) production and/or a suppressive activity on the production of inflammatory cytokines such as TNF-α, IL-1, IL-6 and the like, which is useful as an agent for the prophylaxis and treatment of diseases such as cardiac disease, autoimmune disease, inflammatory disease, central nervous system disease, infectious disease, sepsis, septic shock and the like, and a production method thereof and use thereof.

BACKGROUND ART

Nitric oxide (NO) has been reported to play various roles in the physiological activity in the body of mammal; for example, as a vasodilator in the vascular system [Pharmacol. Rev., vol. 43, 109-142 (1991)], as a factor showing tumor cell eradicating activity in the leukocyte system [Curr. Opin. Immunol., vol. 3, 65-70 (1991)], and as a neurotransmitter in the nervous system [Neuron, vol. 8, 3-11 (1992)]. Basically, NO is produced from L-arginine by NO synthase (NOS), and to date, the presence of three kinds of isoforms of genetically nerve NOS, vascular endothelial NOS and inducible NOS (iNOS) has been clarified [Cell, vol. 70, pp. 705-707 (1992)]. Based on the mode of presence, the former two are also referred to as constitutive NOS (cNOS) as contrasted with the latter as iNOS.

The cNOS is considered to be present in the vascular endothelial cell and neurocyte, be calcium calmodulin-dependant, produce a small amount of NO by activation of various receptor stimulations, and to be responsible for the aforementioned physiological control. In contrast, iNOS is known to be induced by various cytokines, bacterial lipopolysaccharides (LPS) and the like to produce a large amount of NO in a sustained manner in macrophage, neutrophile and the like, and to damage and hurt cells and tissues at a production site, while showing the above-mentioned physiological activity [Immunol. Today, vol. 13, 157-160 (1992)]. Known cells and tissues that express iNOS are the aforementioned cells, as well as hepatocyte, kupffer's cell, glia cell, vascular smooth muscle cell, vascular endothelial cell, inner membrane of cardiac muscle, cardiac muscle cell, mesangial cell, chondrocyte, synovial cell, pancreatic β cell, osteoclast and the like [FASEB J., vol. 6, 3051-3064 (1992), Arch Surg., vol. 128, 396-401 (1993), J. Biol. Chem., vol. 44, 27580-27588 (1994), J. Cell. Biochem., vol. 57, 399-408 (1995)].

Heretofore, L-arginine analogs [Pharmacol. Rev., vol. 43, 109-142 (1991)], aminoguanidine [Br. J. Pharmacol., vol. 110, 963-968 (1993)], S-ethylisothiourea [J. Biol. Chem., vol. 43, 26669-26676 (1994)] and the like have been reported to inhibit iNOS.

It is also known that cytokines, such as TNF-α, IL-1, IL-6 and the like, are secreted by various cells such as monocyte, macrophage, lymphocyte, neutrophile, fibroblast, vascular endothelial cell and the like and widely involved in biological defense and immune system based on inflammation [The Cytokine Handbook, 2nd ed Academic Press Limited (1994), Advances Immunol., vol. 62, 257-304 (1996)].

It has been clarified that TNF-α and IL-1 show activities such as (1) fever, (2) activation and promoted chemotaxis of inflammatory cells such as macrophage, neutrophile and the like, (3) induction of inflammatory cytokines such as IL-1, IL-6, IL-8, TNF, CSF and the like and acute protein, (4) promotion of production of various chemical mediators such as NO, $O_2^-$, PAF, prostaglandin, leukotriene, protease and the like; and that IL-6 shows activity such as (1) introduction of acute protein, (2) increasing blood platelet, (3) differentiation and activation of lymphocyte and NK cell, (4) growth of osteoclast, and the like. However, excess production of these cytokines and production thereof at inappropriate sites and time is inconvenient for organisms. For example, these cytokines have been found to be involved in various diseases such as cachexia, allergic disease, rheumatoid arthritis, abscess, graft rejection, anemia, arteriosclerosis, autoimmune disease, diabetes, central nervous system disease, inflammatory bowel disease, cardiac disease, hepatitis, cirrhosis, nephritis, osteoporosis, psoriasis, septic shock and the like, caused by protozoan, bacteria, fungi, virus, cancer and the like. It has been described that a substance that suppresses or antagonizes production of TNF-α, IL-1, IL-6 and the like can be a therapeutic drug of these diseases [Eur. J. Immunol., vol. 18, 951-956 (1991), Immunol., vol. 83, 262-267 (1994), Proc. Natl. Acad. Sci., vol. 93, 3967-3971 (1997), J. Immunol., vol. 147, 1530-1536 (1991), Immunol. Today, vol. 12, 404-410 (1991)].

Because substances that suppress NO production by iNOS inducible cell, thereby to treat cardiac disease, autoimmune disease, inflammatory disease, septic shock and the like are considered to be effective as a prophylactic and therapeutic drug of various diseases, such as arteriosclerosis, myocarditis, cardiac myopathy, brain ischemic disorder, Alzheimer's disease, multiple sclerosis, septic shock, rheumatoid arthritis, osteoarthritis, gastric ulcer, duodenal ulcer, ulcerative colitis, diabetes, glomerular nephritis, osteoporosis, pneumonia, hepatitis, psoriasis, graft rejection, pain and the like, and because the cells targeted by cytokines are diversified over, for example, the inflammation system, the vascular system, the central nervous system, the hematopoietic system, the endocrine system and the like, the biological activities thereof are considered to be diversified, too. These compounds, however, are not entirely satisfactory from the aspect of activity, and are associated with problems that they inhibit not only iNOS but also cNOS responsible for physiological activity, and the like. Therefore, the invention provides an improved agent for the prophylaxis or treatment of diseases such as cardiac disease, autoimmune disease, inflammatory disease, septic shock and the like.

DISCLOSURE OF THE INVENTION

In view of the current situation, the present inventors have conducted researches and study of an agent for the prophylaxis or treatment of the aforementioned diseases, which suppresses NO production from iNOS inducible cells and/or production of inflammatory cytokines, and synthesized, for the first time, a compound of the formula:

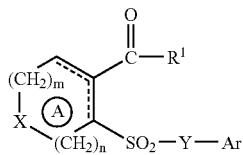
(I)

wherein

R[1] is an optionally substituted aliphatic hydrocarbon group, an optionally substituted aromatic hydrocarbon group, an optionally substituted heterocyclic group, a group of the formula: OR[1a] wherein R[1a] is a hydrogen atom or an optionally substituted aliphatic hydrocarbon group, or a group of the formula:

(a)

wherein R[1b] and R[2c] are the same or different and each is a hydrogen atom or an optionally substituted aliphatic hydrocarbon group;

X is a methylene group, a nitrogen atom, a sulfur atom or an oxygen atom;

Y is an optionally substituted methylene group or an optionally substituted nitrogen atom; and ring A is a 5 to 8-membered ring optionally substituted further by 1 to 4 substituent(s) selected from the following (1) to (4):

(1) an optionally substituted aliphatic hydrocarbon group,
(2) an optionally substituted aromatic hydrocarbon group,
(3) a group of the formula: OR[2] wherein R[2] is a hydrogen atom or an optionally substituted aliphatic hydrocarbon group and
(4) a halogen atom;

Ar is an optionally substituted aromatic hydrocarbon group;
a group of the formula:

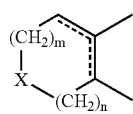
(b)

is a group of the formula:

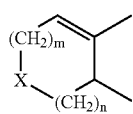
(b1)

or the formula:

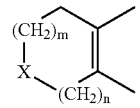
(b2)

m is an integer of 0 to 2; and n is an integer of 1 to 3 where the sum of m and n is not more than 4, provided that when X is a methylene group, Y is an optionally substituted methylene group, and a salt thereof, which are characterized by a chemical structure where at least one of a carboxylic acid ester group or carbonyl group, and a sulfonamide group or sulfonyl group is substituted at a constituent carbon of

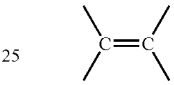

and the both are substituted at two adjacent cycloalkene-constituting carbons, and found that the obtained compound unexpectedly has, based on its chemical structure, a superior inhibitory activity on NO and/or cytokine production and the like, has a superior action of inhibiting not only NO production from iNOS inducible cell but also production of inflammatory cytokines, can be a prophylactic and therapeutic agent more effective than conventional drugs, and that the compound has superior properties of a clinically useful pharmaceutical agent against the diseases such as cardiac disease, autoimmune disease, inflammatory disease, septic shock and the like, where inflammatory cytokines, such as TNF-α, IL-1, IL-6 and the like, and NO are considered to not act independently from each other but cause progression of the diseases because of their complicated relationship.

Accordingly, the present invention relates to:

[1] a compound of the formula:

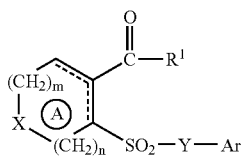
(I)

wherein

R[1] is an optionally substituted aliphatic hydrocarbon group, an optionally substituted aromatic hydrocarbon group, an optionally substituted heterocyclic group, a group of the formula: OR[1a] wherein R[1a] is a hydrogen atom or an optionally substituted aliphatic hydrocarbon group, or a group of the formula:

wherein $R^{1b}$ and $R^{1c}$ are the same or different and each is a hydrogen atom or an optionally substituted aliphatic hydrocarbon group;

X is a methylene group, a nitrogen atom, a sulfur atom or an oxygen atom;

Y is an optionally substituted methylene group or an optionally substituted nitrogen atom; and ring A is a 5 to 8-membered ring optionally substituted further by 1 to 4 substituent(s) selected from the following (1) to (4):

(1) an optionally substituted aliphatic hydrocarbon group,
(2) an optionally substituted aromatic hydrocarbon group,
(3) a group of the formula: $OR^2$ wherein $R^2$ is a hydrogen atom or an optionally substituted aliphatic hydrocarbon group and
(4) a halogen atom;

Ar is an optionally substituted aromatic hydrocarbon group;

a group of the formula:

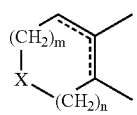

is a group of the formula:

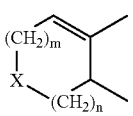

or the formula:

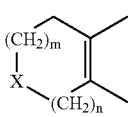

m is an integer of 0 to 2; and n is an integer of 1 to 3 where the sum of m and n is not more than 4 provided that when X is a methylene group, Y is an optionally substituted methylene group, or a salt thereof,

[2] the compound of [1] wherein $R^1$ is (i) an aliphatic hydrocarbon group selected from $C_{1-20}$ alkyl group, $C_{3-10}$ cycloalkyl group, $C_{4-12}$ cycloalkylalkyl group, $C_{3-6}$ alkenyl group and $C_{3-6}$ alkynyl group, wherein these aliphatic hydrocarbon groups optionally have 1 to 4 substituent(s) selected from the group consisting of heterocyclic group, oxo group, hydroxy group, $C_{1-6}$ alkoxy group, $C_{3-10}$ cycloalkyloxy group, $C_{6-10}$ aryloxy group, $C_{7-19}$ aralkyloxy group, heterocyclyloxy group, $C_{1-6}$ alkylthio group (the sulfur atom being optionally oxidized), $C_{3-10}$ cycloalkylthio group (the sulfur atom being optionally oxidized), $C_{6-10}$ arylthio group (the sulfur atom being optionally oxidized), $C_{7-19}$ aralkylthio group (the sulfur atom being optionally oxidized), heterocyclylthio group, heterocyclylsulfinyl group, heterocyclylsulfonyl group, nitro group, halogen atom, cyano group, carboxyl group, $C_{1-10}$ alkoxy-carbonyl group, $C_{3-6}$ cycloalkyloxycarbonyl group, $C_{6-10}$ aryloxy-carbonyl group, $C_{7-19}$ aralkyloxy-carbonyl group, heterocyclic oxycarbonyl group, $C_{6-10}$ arylcarbonyl group, $C_{1-6}$ alkanoyl group, $C_{3-5}$ alkenoyl group, $C_{6-10}$ aryl-carbonyloxy group, $C_{2-6}$ alkanoyloxy group, $C_{3-5}$ alkenoyloxy group, carbamoyl group optionally substituted by 1 or 2 substituent(s) selected from $C_{1-4}$ alkyl, phenyl, $C_{1-7}$ acyl and $C_{1-4}$ alkoxy-phenyl), thiocarbamoyl group (optionally substituted by 1 or 2 substituent(s) selected from $C_{1-4}$ alkyl and phenyl), carbamoyloxy group (optionally substituted by 1 or 2 substituent(s) selected from $C_{1-4}$ alkyl and phenyl), $C_{1-6}$ alkanoylamino group, $C_{6-10}$ aryl-carbonylamino group, $C_{6-10}$ alkoxy-carboxamido group, $C_{6-10}$ aryloxy-carboxamido group, $C_{7-19}$ aralkyloxy-carboxamido group, $C_{1-10}$ alkoxy-carbonyloxy group, $C_{6-10}$ aryloxy-carbonyloxy group, $C_{7-19}$ aralkyloxy-carbonyloxy group, $C_{3-10}$ cycloalkyloxy-carbonyloxy group and ureido group (optionally having 1 to 3 substituent(s) selected from $C_{1-4}$ alkyl group and phenyl group) (hereinafter substituent group A) and a group consisting of $C_{6-10}$ aryl group optionally having 1 to 4 substituent(s) selected from substituent group A (hereinafter substituent group B), the aforementioned heterocyclic group is a 5 to 8-membered heterocyclic group having, besides carbon atoms, 1 to 4 hetero atom(s) selected from a nitrogen atom (optionally oxidized), an oxygen atom and a sulfur atom, or a fused ring thereof, which optionally has 1 to 3 substituent(s) selected from $C_{1-4}$ alkyl, hydroxy, oxo and $C_{1-4}$ alkoxy, and the above-mentioned substituents may form, together with an aliphatic hydrocarbon group, a fused ring optionally having 1 to 4 substituent(s) selected from substituent group B, (ii) $C_{6-14}$ aryl group optionally having 1 to 5 substituent(s) selected from a group consisting of halogen atom, $C_{1-4}$ alkyl group, $C_{1-4}$ alkoxy group, $C_{1-4}$ alkoxy-carbonyl group, carboxyl group, nitro group, cyano group, hydroxy group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group (hereinafter substituent group C), (iii) a 5 to 8-membered heterocyclic ring having, besides carbon atoms, 1 to 4 hetero atom(s) selected from a nitrogen atom (optionally oxidized), an oxygen atom and a sulfur atom, or a fused ring thereof, which heterocyclic group may have 1 to 3 substituent(s) selected from $C_{1-4}$ alkyl, hydroxy, oxo and $C_{1-4}$ alkoxy, (iv) a group of the formula: $OR^{1a}$ wherein $R^{1a}$ is a hydrogen atom or an aliphatic hydrocarbon group selected from $C_{1-20}$ alkyl group, $C_{3-10}$ cycloalkyl group, $C_{4-12}$ cycloalkylalkyl group, $C_{3-6}$ alkenyl group and $C_{3-6}$ alkynyl group optionally having substituent(s) selected from substituent group B, or (v) a group of the formula:

(a)

wherein $R^{1b}$ and $R^{1c}$ are the same or different and each is a hydrogen atom or an aliphatic hydrocarbon group selected from $C_{1-20}$ alkyl group, $C_{3-10}$ cycloalkyl group, $C_{4-12}$ cycloalkylalkyl group, $C_{3-6}$ alkenyl group and $C_{3-6}$ alkynyl group optionally having substituent(s) selected from substituent group B;

X is a methylene group, a nitrogen atom, a sulfur atom or an oxygen atom;

Y is
  (i) a methylene group optionally having substituent(s) selected from $C_{1-6}$ alkyl group, hydroxy substituted-$C_{1-6}$ alkyl group and $C_{1-4}$ alkoxy-carbonyl-$C_{1-4}$ alkyl group or
  (ii) a nitrogen atom optionally having substituent(s) selected from $C_{1-6}$ alkyl group, hydroxy substituted-$C_{1-6}$ alkyl group and $C_{1-4}$ alkoxy-carbonyl-$C_{1-4}$ alkyl group;

ring A is a 5 to 8-membered ring optionally substituted further by 1 to 4 substituent(s) selected from the following (1) to (4):
  (1) an aliphatic hydrocarbon group selected from $C_{1-20}$ alkyl group, $C_{3-10}$ cycloalkyl group, $C_{4-12}$ cycloalkylalkyl group, $C_{3-6}$ alkenyl group and $C_{3-6}$ alkynyl group optionally having substituent(s) selected from substituent group B,
  (2) $C_{6-14}$ aryl group optionally having substituent(s) selected from substituent group C,
  (3) a group of the formula: $OR^2$ wherein $R^2$ is a hydrogen atom, or an aliphatic hydrocarbon group selected from $C_{1-20}$ alkyl group, $C_{3-10}$ cycloalkyl group, $C_{4-12}$ cycloalkylalkyl group, $C_{3-6}$ alkenyl group and $C_{3-6}$ alkynyl group, optionally having substituent(s) selected from substituent group B and
  (4) a halogen atom;

Ar is a $C_{6-14}$ aryl group optionally having substituent(s) selected from substituent group C;

the group of the formula:

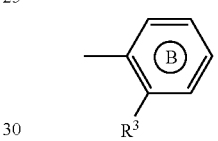
(b)

is a group of the formula:

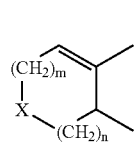
(b1)

or the formula:

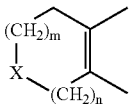
(b2)

m is an integer of 0 to 2; and n is an integer of 1 to 3 where the sum of m and n is not more than 4,

[3] the compound of [1], wherein the ring A is a 5 to 8-membered ring optionally substituted by lower alkyl, phenyl or halogen, $R^1$ is $OR^{1a}$ where $R^{1a}$ is optionally substituted lower alkyl group, and Ar is an optionally substituted phenyl group,

[4] the compound of [3], wherein $R^{1a}$ is an ethyl group,

[5] the compound of [3], wherein Ar is a halogenophenyl group, a lower alkylphenyl group or a phenyl group substituted by halogen and lower alkyl,

[6] the compound of [3], wherein Ar is a group of the formula:

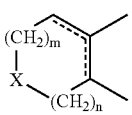
(c)

wherein $R^3$ is a halogen atom or a lower alkyl group and ring B may be further substituted by halogen atom,

[7] the compound of [1], wherein the group of the formula:

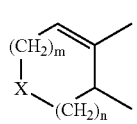
(b)

is a group of the formula:

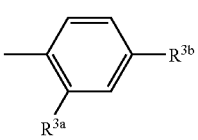
(b1)

[8] the compound of [6], wherein Ar is a group of the formula:

(c1)

wherein $R^{3a}$ and $R^{3b}$ are the same or different and each is a halogen atom,

[9] the compound of [1], wherein $R^1$ is a group represented by $OR^{1a}$ ($R^{1a}$ is a hydrogen atom or an aliphatic hydrocarbon group optionally having substituent(s)), m is 1, and n is 1,

[10] the compound of [1], wherein R$^1$ is a group of the formula: OR$^{1a'}$ (R$^{1a'}$ is a C$_{1-6}$ alkyl group), a group of the formula:

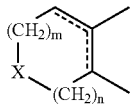
(b)

is a group of the formula:

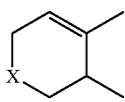

X is methylene or an oxygen atom, Y is methylene or —NH—, Ar is a phenyl group optionally having 1 or 2 substituent(s) selected from the group consisting of halogen atom and C$_{1-6}$ alkoxy,

[11] the compound of [1], wherein R$^1$ is a group of the formula: OR$^{1a'}$ (R$^{1a'}$ is a C$_{1-6}$ alkyl group), a group of the formula:

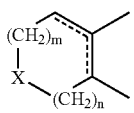
(b)

is a group of the formula:

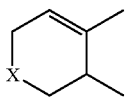

X is methylene and Y is methylene, or X is an oxygen atom and Y is —NH—, and Ar is a phenyl group optionally having two halogen atoms (e.g., 2-chloro-4-fluorophenyl group and the like),

[12] ethyl 6-[(2-chloro-4-fluorobenzyl)sulfonyl]-1-cyclohexene-1-carboxylate, ethyl (+)-6-[(2-chloro-4-fluorobenzyl)sulfonyl]-1-cyclohexene-1-carboxylate or ethyl 3-[(2-chloro-4-fluorophenyl)sulfamoyl]-3,6-dihydro-2H-pyran-4-carboxylate,

[13] a prodrug of the compound of [1],

[14] a production method of a compound of the formula:

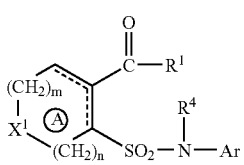
(Ia)

wherein
a group of the formula:

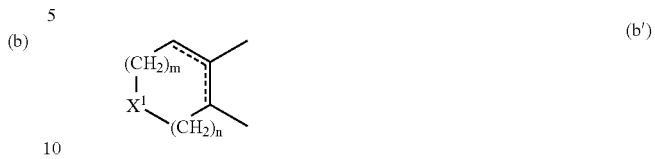
(b')

is a group of the formula:

(b1')

or the formula:

(b2')

R$^1$ is an optionally substituted aliphatic hydrocarbon group, an optionally substituted aromatic hydrocarbon group, an optionally substituted heterocyclic group, a group of the formula: OR$^{1a}$ wherein R$^{1a}$ is a hydrogen atom or an optionally substituted aliphatic hydrocarbon group, or a group of the formula:

(a)

wherein R$^{1b}$ and R$^{1c}$ are the same or different and each is a hydrogen atom, or an optionally substituted aliphatic hydrocarbon group;

X$^1$ is a nitrogen atom, a sulfur atom or an oxygen atom;

ring A is a 5 to 8-membered ring optionally substituted further by 1 to 4 substituent(s) selected from the following (1) to (4):

(1) an optionally substituted aliphatic hydrocarbon group, (2) an optionally substituted aromatic hydrocarbon group, (3) a group of the formula: OR$^2$ wherein R$^2$ is hydrogen atom or an optionally substituted aliphatic hydrocarbon group and (4) a halogen atom;

R$^4$ is a hydrogen atom or an optionally substituted lower alkyl group;

Ar is an optionally substituted aromatic hydrocarbon group;

m is an integer of 0 to 2; and n is an integer of 1 to 3 where the sum of m and n is not more than 4,- or a salt thereof, which method comprises reacting a compound of the formula:

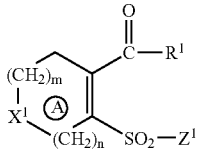

(II)

wherein $Z^1$ is a leaving group and other symbols are as defined above, or a salt thereof, and a compound of the formula:

(III)

wherein each symbol is as defined above, or a salt thereof,

[15] a production method of a compound of the formula:

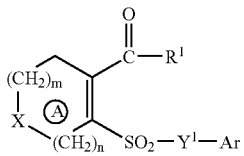

(Ib)

wherein $R^1$ is an optionally substituted aliphatic hydrocarbon group, an optionally substituted aromatic hydrocarbon group, an optionally substituted heterocyclic group, a group of the formula: $OR^{1a}$ wherein $R^{1a}$ is a hydrogen atom or optionally substituted aliphatic hydrocarbon group, or a group of the formula:

(a)

wherein $R^{1b}$ and $R^{1c}$ are the same or different and each is a hydrogen atom, or an optionally substituted aliphatic hydrocarbon group;

X is a methylene group, a nitrogen atom, a sulfur atom or an oxygen atom;

ring A is a 5 to 8-membered ring optionally substituted further by 1 to 4 substituent(s) selected from the following (1) to (4):

(1) an optionally substituted aliphatic hydrocarbon group,
(2) an optionally substituted aromatic hydrocarbon group,
(3) a group of the formula: $OR^2$ wherein $R^2$ is hydrogen atom or an optionally substituted aliphatic hydrocarbon group and
(4) a halogen atom;

$Y^1$ is an optionally substituted methylene group;

Ar is an optionally substituted aromatic hydrocarbon group;

a group of the formula:

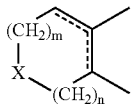

(b)

is a group of the formula:

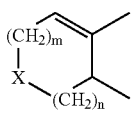

(b1)

or the formula:

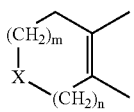

(b2)

m is an integer of 0 to 2; and n is an integer of 1 to 3 where the sum of m and n is not more than 4, or a salt thereof, which method comprises reacting a compound of the formula:

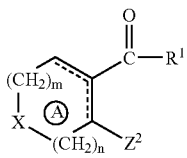

(IV)

wherein $Z^2$ is a leaving group, and other symbols are as defined above, or a salt thereof, and a compound of the formula:

HS—$Y^1$—Ar  (VI)

wherein each symbol is as defined above, or a salt thereof, and oxidizing the obtained sulfide,

[16] a pharmaceutical composition containing a compound of the formula:

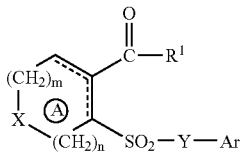

(I)

wherein $R^1$ is an optionally substituted aliphatic hydrocarbon group, an optionally substituted aromatic hydrocarbon group, an optionally substituted heterocyclic group, a group of the formula: $OR^{1a}$ wherein $R^{1a}$ is a hydrogen atom or an optionally substituted aliphatic hydrocarbon group, or a group of the formula:

(a)

wherein $R^{1b}$ and $R^{1c}$ are the same or different and each is a hydrogen atom or an aliphatic hydrocarbon group optionally having substituent(s);

X is a methylene group, a nitrogen atom, a sulfur atom or an oxygen atom;

Y is an optionally substituted methylene group or an optionally substituted nitrogen atom; and ring A is a 5 to 8-membered ring optionally substituted further by 1 to 4 substituent(s) selected from the following (1) to (4):
(1) an optionally substituted aliphatic hydrocarbon group,
(2) an optionally substituted aromatic hydrocarbon group,
(3) a group of the formula: $OR^2$ wherein $R^2$ is a hydrogen atom or an optionally substituted aliphatic hydrocarbon group and
(4) a halogen atom;

Ar is an optionally substituted aromatic hydrocarbon group; a group of the formula:

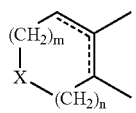
(b)

is a group of the formula:

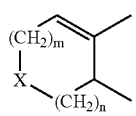
(b1)

or the formula:

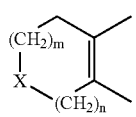
(b2)

m is an integer of 0 to 2; and
n is an integer of 1 to 3 where the sum of m and n is not more than 4,
   provided that when X is a methylene group, Y is an optionally substituted methylene group, a salt thereof, or a prodrug thereof,

[17] the pharmaceutical composition of [16], which is an agent for suppressing nitric oxide (NO) and/or cytokine production,

[18] the pharmaceutical composition of [16], which is an agent for the prophylaxis or treatment of a cardiac disease, an autoimmune disease or septic shock,

[19] a method for suppressing nitric oxide (NO) and/or cytokine production, which method comprising administering an effective amount of the compound of [1] or a prodrug thereof to a mammal,

[20] a method for the treatment of a cardiac disease, an autoimmune disease or septic shock, which method comprising administering an effective amount of the compound of [1] or a prodrug thereof to a mammal,

[21] use of the compound of [1] or a prodrug thereof for the production of an agent for suppressing nitric oxide (NO) and/or cytokine production, and

[22] use of the compound of [1] or a prodrug thereof for the production of an agent for the prophylaxis or treatment of a cardiac disease, an autoimmune disease or septic shock.

BEST MODE FOR EMBODYING THE INVENTION

In the present specification, $R^1$ is an aliphatic hydrocarbon group optionally having substituent(s), an aromatic hydrocarbon group optionally having substituent(s), an heterocyclic group optionally having substituent(s), a group of the formula: $OR^{1a}$, or a group of the formula (a). Particularly, a group of the formula: $OR^{1a}$ is preferable.

As the "aliphatic hydrocarbon group" of the "aliphatic hydrocarbon group optionally having substituent(s)" represented by $R^1$, for example, alkyl group, cycloalkyl group, cycloalkylalkyl group, alkenyl group, alkynyl group and the like are preferable.

As the alkyl group, for example, straight chain or branched alkyl group having 1 to 20 carbon atoms (e.g., methyl group, ethyl group, n-propyl group, isopropyl group, n-butyl group, isobutyl group, sec-butyl group, tert-butyl group, pentyl group, hexyl group, heptyl group, octyl group, nonyl group, decyl group, dodecyl group and the like) and the like are preferable. For example, lower alkyl group having 1 to 6 carbon atoms (e.g., methyl group, ethyl group, n-propyl group, isopropyl group, n-butyl group, isobutyl group, sec-butyl group, tert-butyl group and the like) and the like are particularly preferable.

As the cycloalkyl group, for example, cycloalkyl group having 3 to 10 carbon atoms (e.g., cyclopropyl group, cyclobutyl group, cyclopentyl group, cyclohexyl group, cycloheptyl group, cyclooctyl group and the like) and the like are preferable. For example, cycloalkyl group having 3 to 6 carbon atoms (e.g., cyclopropyl group, cyclobutyl group, cyclopentyl group, cyclohexyl group and the like) and the like are particularly preferable.

As the cycloalkylalkyl group, for example, cycloalkylalkyl group having 4 to 12 carbon atoms (e.g., cyclopropylmethyl group, cyclopentylmethyl group, cyclohexylmethyl group, cycloheptylmethyl group and the like) and the like are preferable. For example, cycloalkylalkyl group having 4 to 8 (particularly 4 to 7) carbon atoms (e.g., cyclopropylmethyl group, cyclopentylmethyl group, cyclohexylmethyl group and the like), and the like are particularly preferable.

As the alkenyl group, for example, lower alkenyl group having 3 to 6 carbon atoms (e.g., propenyl group, butenyl group, pentenyl group and the like) and the like are preferable. For example, lower alkenyl group having 3 or 4 carbon atoms (e.g., propenyl group, butenyl group and the like) and the like are particularly preferable.

As the alkynyl group, for example, lower alkynyl group having 3 to 6 carbon atoms (e.g., propynyl group, butynyl group, pentynyl group and the like) and the like are preferable. For example, lower alkynyl group having 3 or 4 carbon atoms (e.g., propynyl group, butynyl group and the like) and the like are particularly preferable.

As the aforementioned "substituent" of the "aliphatic hydrocarbon group optionally having substituent(s)", for example, heterocyclic group, oxo group, hydroxy group, $C_{1-6}$ alkoxy group, $C_{3-10}$ (particularly $C_{3-6}$) cycloalkyloxy group, $C_{6-10}$ aryloxy group, $C_{7-19}$ (particularly $C_{7-12}$) aralkyloxy group, heterocyclyloxy group, $C_{1-6}$ alkylthio group (the sulfur atom being optionally oxidized), $C_{3-10}$ (particularly $C_{3-6}$) cycloalkylthio group (the sulfur atom being optionally oxidized), $C_{6-10}$ arylthio group (the sulfur atom being optionally oxidized), $C_{7-19}$ (particularly $C_{7-12}$) aralkylthio group (the sulfur atom being optionally oxidized), heterocyclic thio group, heterocyclic sulfinyl group, heterocyclic sulfonyl group, nitro group, halogen atom, cyano group, carboxyl group, $C_{1-10}$ (particularly $C_{1-6}$) alkoxy-carbonyl group, $C_{3-6}$ cycloalkyloxy-carbonyl group, $C_{6-10}$ aryloxy-carbonyl group, $C_{7-19}$, (particularly $C_{7-12}$) aralkyloxy-carbonyl group, heterocyclic oxycarbonyl group, $C_{6-10}$ aryl-carbonyl group, $C_{1-6}$ alkanoyl group, $C_{3-5}$ alkenoyl group, $C_{6-10}$ aryl-carbonyloxy group, $C_{2-6}$alkanoyloxy group, $C_{3-5}$ alkenoyloxy group, optionally substituted carbamoyl group, optionally substituted thiocarbamoyl group, optionally substituted carbamoyloxy group, $C_{1-6}$ alkanoylamino group, $C_{6-10}$ aryl-carbonylamino group, $C_{1-10}$ (particularly $C_{1-6}$) alkoxy-carboxamido group, $C_{6-10}$ aryloxy-carboxamido group, $C_{7-19}$ (particularly $C_{7-12}$)aralkyloxy-carboxamido group, $C_{1-10}$ (particularly $C_{1-6}$) alkoxy-carbonyloxy group, $C_{6-10}$ aryloxy-carbonyloxy group, $C_{7-19}$ (particularly $C_{7-12}$) aralkyloxy-carbonyloxy group, $C_{3-10}$ (particularly $C_{3-6}$) cycloalkyloxy-carbonyloxy group, optionally substituted ureido group, optionally substituted $C_{6-10}$ aryl group and the like are used.

These substituents are substituted at substitutable positions of the aforementioned "aliphatic hydrocarbon group". The substituent is not limited to one but may be in plurality (2 to 4), which may be the same or different.

As the "$C_{1-6}$ alkoxy group", for example, methoxy group, ethoxy group, n-propoxy group, isopropoxy group, n-butoxy group, tert-butoxy group, n-pentyloxy group, n-hexyloxy group and the like are preferable; as the "$C_{3-10}$ cycloalkyloxy group", for example, cyclopropyloxy group, cyclohexyloxy group and the like are preferable; as the "$C_{6-10}$ aryloxy group", for example, phenoxy group, naphthyloxy group and the like are preferable; as the "$C_{7-19}$ aralkyloxy group", for example, benzyloxy group, 1-phenylethyloxy group, 2-phenylethyloxy group, benzhydryloxy group, 1-naphthylmethyloxy group and the like are preferable; as the "$C_{1-6}$ alkylthio group (the sulfur atom being optionally oxidized)", for example, methylthio group, ethylthio group, n-propylthio group, n-butylthio group, methylsulfinyl group, methylsulfonyl group and the like are preferable; as the "$C_{3-10}$ cycloalkylthio group (the sulfur atom being optionally oxidized)", for example, cyclopropylthio group, cyclohexylthio group, cyclopentylsulfinyl group, cyclohexylsulfonyl group and the like are preferable; as the "$C_{6-10}$ arylthio group (the sulfur atom being optionally oxidized)", for example, phenylthio group, naphthylthio group, phenylsulfinyl group, phenylsulfonyl group and the like are preferable; as the "$C_{7-19}$ aralkylthio group (the sulfur atom being optionally oxidized)", for example, benzylthio group, phenylethylthio group, benzhydrylthio group, benzylsulfinyl group, benzylsulfonyl group and the like are preferable; as the "halogen atom", for example, fluorine atom, chlorine atom, bromine atom, iodine atom and the like are preferable; as the "$C_{3-10}$ alkoxy-carbonyl group", for example, methoxycarbonyl group, ethoxycarbonyl group, n-propoxycarbonyl group, isopropoxycarbonyl group, n-butoxycarbonyl group, isobutoxycarbonyl group, tert-butoxycarbonyl group and the like are preferable; as the "$C_{3-6}$ cycloalkyloxycarbonyl group", for example, cyclopropyloxycarbonyl group, cyclopentyloxycarbonyl group, cyclohexyloxycarbonyl group, norbornyloxycarbonyl group and the like are preferable; as the "$C_{6-10}$ aryloxy-carbonyl group", for example, phenoxycarbonyl group, naphthyloxycarbonyl group and the like are preferable; as the "$C_{7-19}$ aralkyloxy-carbonyl group", for example, benzyloxycarbonyl group, benzhydryloxycarbonyl group, 2-phenethyloxycarbonyl group and the like are preferable; as the "$C_{6-10}$ aryl-carbonyl group", for example, benzoyl group, naphthoyl group, phenylacetyl group and the like are preferable; as the "$C_{1-6}$ alkanoyl group", for example, formyl group, acetyl group, propionyl group, butyryl group, valeryl group, pivaloyl group and the like are preferable; and as the "$C_{3-5}$ alkenoyl group", for example, acryloyl group, crotonoyl group and the like are preferable; as the "$C_{6-10}$ aryl-carbonyloxy group", for example, benzoyloxy group, naphthoyloxy group, phenylacetoxy group and the like are preferable; as the "$C_{2-6}$alkanoyloxy group", for example, acetoxy group, propionyloxy group, butyryloxy group, valeryloxy group, pivaloyloxy group and the like are preferable; as the "$C_{3-5}$ alkenoyloxy group", for example, acryloyloxy group, crotonoyloxy group and the like are preferable.

As the "optionally substituted carbamoyl group", for example, carbamoyl group, cyclic aminocarbonyl group and the like optionally substituted by 1 or 2 substituent(s) selected from $C_{1-4}$ alkyl (e.g., methyl, ethyl and the like), phenyl, $C_{1-7}$ acyl (e.g., acetyl, propionyl, benzoyl and the like), $C_{1-4}$ alkoxy-phenyl (e.g., methoxyphenyl and the like) and the like are used, which is specifically, for example, carbamoyl group, N-methylcarbamoyl group, N-ethylcarbamoyl group, N,N-dimethylcarbamoyl group, N,N-diethylcarbamoyl group, N-phenylcarbamoyl group, N-acetylcarbamoyl group, N-benzoylcarbamoyl group, N-(p-methoxyphenyl)carbamoyl group, 1-pyrrolidinylcarbonyl group, piperidinocarbonyl group, 1-piperazinylcarbonyl group, morpholinocarbonyl group and the like. As the "optionally substituted thiocarbamoyl group", for example, thiocarbamoyl group optionally substituted by 1 or 2 substituent(s) selected from $C_{1-4}$ alkyl (e.g., methyl, ethyl and the like), phenyl and the like is used, which is specifically, for example, thiocarbamoyl group, N-methylthiocarbamoyl group, N-phenylthiocarbamoyl group and the like. As the "optionally substituted carbamoyloxy group", for example, carbamoyloxy group optionally substituted by 1 or 2 substituent(s) selected from $C_{1-4}$ alkyl (e.g., methyl, ethyl and the like), phenyl and the like are used, which is specifically, for example, carbamoyloxy group, N-methylcarbamoyloxy group, N,N-dimethylcarbamoyloxy group, N-ethylcarbamoyloxy group, N-phenylcarbamoyloxy group and the like.

As the "$C_{1-6}$ alkanoylamino group", for example, acetamido group, propionamido group, butyramido group, valeramido group, pivalamido group and the like are used; as the "$C_{6-10}$ aryl-carbonylamino group", for example, benzamido group, naphtamido group, phthalimido group and the like are used; as the "$C_{1-10}$ alkoxy-carboxamide group", for example, methoxycarboxamido group ($CH_3OCONH-$), ethoxycarboxamido group, tert-butoxycarboxamido group and the like are used; as the "$C_{6-10}$ aryloxy-carboxamido group", for example, phenoxycarboxamido group ($C_6H_5OCONH-$) and the like are used; as the "$C_{7-10}$ aralkyloxy-carboxamido group", for example, benzyloxycarboxamido group ($C_6H_5CH_2OCONH-$), benzhydryloxycarboxamido group and the like are used; as the "$C_{1-10}$ alkoxy-carbonyloxy group", for example, methoxycarbonyloxy group, ethoxycarbonyloxy group, n-propoxycarbonyloxy group, isopropoxycarbonyloxy group, n-butoxycarbonyloxy group, tert-butoxycarbonyloxy group, n-pentyloxycarbonyloxy group, n-hexyloxycarbonyloxy group and the like are used; as the "$C_{6-10}$ aryloxy-carbonyloxy group", for example, phenoxycarbonyloxy group, naphthyloxycarbonyloxy group and the like are used; as the "$C_{7-19}$ aralkyloxy-carbonyloxy group", for example, benzyloxycarbonyloxy group, 1-phenylethyloxycarbonyloxy group, 2-phenylethyloxycarbonyloxy group, benzhydryloxycarbonyloxy group and the like are used; and as the "$C_{3-10}$ cycloalkyloxy-carbonyloxy group", for example, cyclopropyloxycarbonyloxy group, cyclohexyloxycarbonyloxy group and the like are used.

As the "optionally substituted ureido group", for example, ureido group optionally substituted by 1 to 3 (particularly 1 or 2) substituent(s) selected from $C_{1-4}$ alkyl (e.g., methyl, ethyl and the like), phenyl and the like is used. Examples thereof include ureido group, 1-methylureido group, 3-methylureido group, 3,3-dimethylureido group, 1,3-dimethylureido group, 3-phenylureido group and the like.

When heterocyclic group, heterocyclic oxy group, heterocyclic thio group, heterocyclic sulfinyl group, heterocyclic sulfonyl group or heterocyclic oxycarbonyl group is used as the "substituent" of the "aliphatic hydrocarbon group optionally having substituent(s)", the heterocyclic group means a group obtained by removing one of hydrogen atoms linked to the heterocyclic ring. Examples thereof include 5 to 8-membered ring (particularly 5 to 6-membered ring) containing 1 to several, preferably 1 to 4, hetero atom(s) such as nitrogen atom (optionally oxidized), oxygen atom, sulfur atom and the like, or a fused ring thereof. Examples of heterocyclic group include pyrrolyl group, pyrazolyl group, imidazolyl group, 1,2,3-triazolyl group, 1,2,4-triazolyl group, tetrazolyl group, furyl group, thienyl group, oxazolyl group, isoxazolyl group, 1,2,3-oxadiazolyl group, 1,2,4-oxadiazolyl group, 1,2,5-oxadiazolyl group, 1,3,4-oxadiazolyl group, thiazolyl group, isothiazolyl group, 1,2,3-thiadiazolyl group, 1,2,4-thiadiazolyl group, 1,2,5-thiadiazolyl group, 1,3,4-thiadiazolyl group, pyridyl group, pyridazinyl group, pyrimidinyl group, pyrazinyl group, indolyl group, pyranyl group, thiopyranyl group, dioxynyl group, dioxolyl group, quinolyl group, pyrido[2,3-d]pyrimidyl group, 1,5-, 1,6-, 1,7-, 1,8-, 2,6- or 2,7-naphthyridyl group, thieno[2,3-d]pyridyl group, benzopyranyl group, tetrahydrofuryl group, tetrahydropyranyl group, dioxolanyl group, dioxanyl group and the like.

These heterocyclic groups may be substituted by 1 to 3 substituent(s) selected from $C_{1-4}$ alkyl (e.g., methyl, ethyl and the like), hydroxy, oxo, $C_{1-4}$ alkoxy (e.g., methoxy, ethoxy and the like) and the like at substitutable position(s).

As the "$C_{6-10}$ aryl group" of the "optionally substituted $C_{6-10}$ aryl group", for example, phenyl group, naphthyl group and the like are used. The $C_{6-10}$ aryl group may be substituted by substituent(s) selected from the "substituents" of the aforementioned "aliphatic hydrocarbon group optionally having substituent(s)" (except optionally substituted $C_{6-10}$ aryl group) at substitutable position (s). Such substituents are substituted at substitutable position(s) of the $C_{6-10}$ aryl group. The substituent is not limited to one but may be in plurality (2 to 4), which may be the same or different.

With regard to the "aliphatic hydrocarbon group optionally having substituent(s)", the substituent may form, together with aliphatic hydrocarbon group, an optionally substituted fused ring. As such fused ring, indanyl group, 1,2,3,4-tetrahydronaphthyl group and the like are used. This fused ring may be substituted by substituent(s) selected from the "substituents" of the aforementioned "aliphatic hydrocarbon group optionally having substituent(s)" and optionally substituted at substitutable position(s). These substituents are substituted at substitutable positions of the fused ring, wherein the substituent is not limited to one but may be in plurality (2 to 4), which may be the same or different.

As the "aromatic hydrocarbon group" of the "aromatic hydrocarbon group optionally having substituent(s)" represented by $R^1$, aromatic hydrocarbon group having 6 to 14 carbon atoms (e.g., phenyl group, naphthyl group, biphenyl group, anthryl group, indenyl group and the like) and the like are preferable. Among others, for example, aryl group having 6 to 10 carbon atoms (e.g., phenyl group, naphthyl group and the like) and the like are preferable. Of these, phenyl group and the like are particularly preferable.

As the "substituent" of the "aromatic hydrocarbon group optionally having substituent(s)" represented by $R^1$, for example, halogen atom (e.g., fluorine, chlorine, bromine, iodine and the like), lower ($C_{1-4}$)alkyl group (e.g., methyl group, ethyl group, propyl group, butyl group and the like), lower ($C_{1-4}$)alkoxy group (e.g., methoxy group, ethoxy group, propoxy group, butoxy group and the like), lower ($C_{1-4}$)alkoxy-carbonyl group (e.g., methoxycarbonyl group, ethoxycarbonyl group, propoxycarbonyl group, butoxycarbonyl group and the like), carboxyl group, nitro group, cyano group, hydroxy group, acylamino group (e.g., alkanoylamino group having 1 to 4 carbon atom(s) such as acetylamino group, propionylamino group, butyrylamino group and the like, and the like), cycloalkyl group having 3 to 6 carbon atoms (e.g., cyclopropyl group, cyclopentyl group and the like), aryl group having 6 to 10 carbon atoms (e.g., phenyl group, naphthyl group, indenyl group and the like), halogeno lower ($C_{1-4}$)alkyl group (e.g., trifluoromethyl group, trifluoroethyl group and the like), halogeno lower ($C_{1-4}$)alkoxy group (e.g., trifluoromethoxy group, 1,1,2,2-tetrafluoroethoxy group, 2,2,3,3,3-pentafluoropropoxy group and the like), lower ($C_{1-4}$)alkylthio group (e.g., methylthio group, ethylthio group, propionylthio group and the like), lower ($C_{1-4}$)alkylsulfonyl group (e.g., methanesulfonyl group, ethanesulfonyl group, propanesulfonyl group and the like), lower ($C_{1-4}$)alkanoyl group (e.g., formyl group, acetyl group, propionyl group and the like), 5-membered aromatic heterocyclic group (e.g., 1,2,3-triazolyl group, 1,2,4-triazolyl group, tetrazolyl group, thiazolyl group, isothiazolyl group, oxazolyl group, isoxazolyl group, thiadiazolyl group, thienyl group, furyl group and the like), carbamoyl group, lower ($C_{1-4}$)alkyl-carbamoyl group (e.g., methylcarbamoyl group, dimethylcarbamoyl group, propionylcarbamoyl group and the like), lower ($C_{1-4}$)alkoxy-carbonyl-lower ($C_{1-4}$)alkyl-carbamoyl group (e.g., butoxycarbonylmethylcarbamoyl group, ethoxycarbonylmethylcarbamoyl group and the like), 1,3-diacylguanidino-lower ($C_{1-4}$)alkyl group (e.g., 1,3-diacetylguanidinomethyl group, 1,3-bis-tert-butoxycarbonylguanidinomethyl group and the like) and the like are used, with preference given to halogen atom (e.g., fluorine atom, chlorine atom, bromine atom, iodine atom and the like), lower ($C_{1-4}$)alkyl group (e.g., methyl group, ethyl group, propyl group, butyl group and the like) and the like, and more preference given to fluorine atom, chlorine atom and methyl group.

These substituents are substituted at substitutable positions of the aromatic hydrocarbon, wherein the number of the substituent is preferably 1 to 5, more preferably 1 to 3, most preferably 1 or 2. When two or more substituents are present, they may be the same or different.

The "heterocyclic group" of the "heterocyclic group optionally having substituent(s)" represented by $R^1$ is, for example, a 5 to 8-membered ring (particularly 5 to 6-membered ring) containing 1 to several, preferably 1 to 4, hetero atom(s) from nitrogen atom (optionally oxidized), oxygen atom, sulfur atom and the like, or a fused ring thereof. These heterocyclic groups are, for example, pyrrolyl group, pyrazolyl group, imidazolyl group, 1,2,3-triazolyl group, 1,2,4-triazolyl group, tetrazolyl group, furyl group, thienyl group, oxazolyl group, isoxazolyl group, 1,2,3-oxadiazolyl group, 1,2,4-oxadiazolyl group, 1,2,5-oxadiazolyl group, 1,3,4-oxadiazolyl group, thiazolyl group, isothiazolyl group, 1,2,3-thiadiazolyl group, 1,2,4-thiadiazolyl group, 1,2,5-thiadiazolyl group, 1,3,4-thiadiazolyl group, pyridyl group, pyridazinyl group, pyrimidinyl group, pyrazinyl group, indolyl group, pyranyl group, thiopyranyl group, dioxinyl group, dioxolyl group, quinolyl group, pyrido[2,3-d]pyrimidyl group, 1,5-, 1,6-, 1,7-, 1,8-, 2,6- or 2,7-naphthyridyl group, thieno[2,3-d]pyridyl group, benzopyranyl group, tetrahydrofuryl group, tetrahydropyranyl group, dioxolanyl group, dioxanyl group and the like. These heterocyclic groups may be substituted by 1 to 3 substituent(s) selected from $C_{1-4}$ alkyl (e.g., methyl, ethyl and the like), hydroxy, oxo, $C_{1-4}$ alkoxy group (e.g., methoxy, ethoxy and the like) and the like at substitutable position(s).

As the "aliphatic hydrocarbon group optionally having substituent(s)" represented by $R^{1a}$, for example, those similar to the aforementioned "aliphatic hydrocarbon group optionally having substituent(s)" represented by $R^1$ can be used. As $R^{1a}$, for example, optionally substituted lower alkyl group having 1 to 6 carbon atom(s) (e.g., methyl group, ethyl group, n-propyl group, isopropyl group, n-butyl group, isobutyl group, tert-butoxycarbonylmethyl group, hydroxyethyl group and the like) and the like are preferably used. Of these, for example, methyl group, ethyl group, n-propyl group, isopropyl group, n-butyl group, isobutyl group and the like are preferably used. Particularly, for example, methyl group, ethyl group, n-propyl group and the like are preferable, and ethyl group and the like are specifically preferable.

As the "aliphatic hydrocarbon group optionally having substituent(s)" represented by $R^{1b}$ and $R^{1c}$, for example, those similar to the aforementioned "aliphatic hydrocarbon group optionally having substituent(s)" represented by $R^1$ can be used. As $R^{1b}$ and $R^{1c}$, for example, optionally substituted lower alkyl group having 1 to 6 carbon atom(s) (e.g., methyl group, ethyl group, n-propyl group, isopropyl group, n-butyl group, isobutyl group, tert-butoxycarbonylmethyl group, hydroxyethyl group and the like) and the like are preferably used. Of these, for example, methyl group, ethyl group, n-propyl group, isopropyl group, n-butyl group, isobutyl group and the like are preferable. Particularly, for example, methyl group, ethyl group, n-propyl group and the like are preferable, and ethyl group and the like are specifically preferable.

As $R^1$, for example, optionally substituted lower alkyl group having 1 to 6 carbon atom(s) (e.g., methyl group, ethyl group, n-propyl group, isopropyl group, n-butyl group, isobutyl group, tert-butoxycarbonylmethyl group, hydroxyethyl group and the like) and the like are preferably used. Of these, for example, methyl group, ethyl group, n-propyl group, isopropyl group, n-butyl group, isobutyl group and the like are preferably used. Particularly, for example, methyl group, ethyl group, n-propyl group and the like are preferable, and ethyl group and the like are specifically preferable.

As the substituent of the optionally substituted methylene group represented by Y, there are mentioned, for example, $C_{1-6}$ alkyl group such as methyl group, ethyl group, n-propyl group, isopropyl group, n-butyl group, isobutyl group and the like, for example, hydroxy substituted-$C_{1-6}$ alkyl group such as hydroxymethyl group, hydroxyethyl group and the like, for example, $C_{1-4}$ alkoxy-carbonyl-$C_{1-4}$ alkyl group such as methoxycarbonylmethyl group, ethoxycarbonylmethyl group, tert-butoxycarbonylmethyl group, methoxycarbonylethyl group, ethoxycarbonylethyl group, tert-butoxycarbonylethyl group and the like, and the like, with preference given to hydrogen atom and methyl group, and particularly hydrogen atom is preferable.

As the substituent of the optionally substituted nitrogen atom represented by Y, there are mentioned, for example, $C_{1-6}$ alkyl group such as methyl group, ethyl group, n-propyl group, isopropyl group, n-butyl group, isobutyl group and the like, for example, hydroxy substituted-$C_{1-6}$ alkyl group such as hydroxymethyl group, hydroxyethyl group and the like, for example, $C_{1-4}$ alkoxy-carbonyl-$C_{1-4}$ alkyl group such as methoxycarbonylmethyl group, ethoxycarbonylmethyl group, tert-butoxycarbonylmethyl group, methoxycarbonylethyl group, ethoxycarbonylethyl group, tert-butoxycarbonylethyl group and the like, and the like. Of these, hydrogen atom and methyl group are preferable, and particularly hydrogen atom is preferable.

As the "aromatic hydrocarbon group" of the "aromatic hydrocarbon group optionally having substituent(s)" represented by Ar, there are mentioned, for example, aromatic hydrocarbon group having 6 to 14 carbon atoms (e.g., phenyl group, naphthyl group, biphenyl group, anthryl group, indenyl group and the like) and the like. Of these, for example, aryl group having 6 to 10 carbon atoms (e.g., phenyl group, naphthyl group and the like) and the like are preferable, and phenyl group and the like are particularly preferable.

As the "substituent" of the "aromatic hydrocarbon group optionally having substituent(s)" represented by Ar, for example, halogen atom (e.g., fluorine, chlorine, bromine, iodine and the like), lower ($C_{1-4}$)alkyl group (e.g., methyl group, ethyl group, propyl group, butyl group and the like), lower ($C_{1-4}$)alkoxy group (e.g., methoxy group, ethoxy group, propoxy group, butoxy group and the like), lower ($C_{1-4}$)alkoxy-carbonyl group (e.g., methoxycarbonyl group, ethoxycarbonyl group, propoxycarbonyl group, butoxycarbonyl group and the like), carboxyl group, nitro group, cyano group, hydroxy group, acylamino group (e.g., alkanoylamino group having 1 to 4 carbon atom(s) such as acetylamino group, propionylamino group, butyrylamino group and the like, and the like), cycloalkyl group having 3 to 6 carbon atoms (e.g., cyclopropyl group, cyclopentyl group and the like), aryl group having 6 to 10 carbon atoms (e.g., phenyl group, naphthyl group, indenyl group and the like), halogeno lower ($C_{1-4}$)alkyl group (e.g., trifluoromethyl group, trifluoroethyl group and the like), halogeno lower ($C_{1-4}$)alkoxy group (e.g., trifluoromethoxy group, 1,1,2,2-tetrafluoroethoxy group, 2,2,3,3,3-pentafluoropropoxy group and the like), lower ($C_{1-4}$)alkylthio group (e.g., methylthio group, ethylthio group, propionylthio group and the like), lower ($C_{1-4}$)alkylsulfonyl group (e.g., methanesulfonyl group, ethanesulfonyl group, propanesulfonyl group and the like), lower ($C_{1-4}$)alkanoyl group (e.g., formyl group, acetyl group, propionyl group and the like), 5-membered aromatic heterocyclic group (e.g., 1,2,3-triazolyl group, 1,2,4-triazolyl group, tetrazolyl group, thiazolyl group, isothiazolyl group, oxazolyl group, isoxazolyl group, thiadiazolyl group, thienyl group, furyl group and the like), carbamoyl group, lower ($C_{1-4}$)alkyl-carbamoyl group (e.g., methylcarbamoyl group, dimethylcarbamoyl group, propionylcarbamoyl group and the like), lower ($C_{1-4}$)alkoxy-carbonyl-lower ($C_{1-4}$)alkyl-carbamoyl group (e.g., butoxycarbonylmethylcarbamoyl group, ethoxycarbonylmethylcarbamoyl group and the like), 1,3-diacylguanidino-lower ($C_{1-4}$)alkyl group (e.g., 1,3-diacetylguanidinomethyl group, 1,3-bis-tert-butoxycarbonylguanidinomethyl group and the like) and the like can be used. Preferably, halogen atom (e.g., fluorine atom, chlorine atom, bromine atom, iodine atom and the like), lower ($C_{1-4}$) alkyl group (e.g., methyl group, ethyl group, propyl group, butyl group and the like) and the like are used and more preferably, fluorine atom, chlorine atom and methyl group are used.

These substituents are substituted at substitutable positions of the aromatic hydrocarbon group, where the number of the substituent is preferably 1 to 5, more preferably 1 to 3, and particularly preferably 1 or 2. When two or more substituents are present, they may be the same or different.

As Ar, for example, phenyl group, halogeno phenyl group, lower ($C_{1-4}$)alkyl-phenyl group, lower ($C_{1-4}$)alkoxy-phenyl group, lower ($C_{1-4}$)alkoxy-carbonylphenyl group, carboxylphenyl group, nitrophenyl group, cyanophenyl group, halogeno lower ($C_{1-4}$)alkyl-phenyl group, halogeno lower ($C_{1-4}$)alkoxy-phenyl group, lower ($C_{1-4}$)alkanoyl-phenyl group, phenyl group substituted by 5-membered aromatic heterocyclic group, lower ($C_{1-4}$)alkoxy-carbonyl-lower ($C_{1-4}$)alkyl-carbamoylphenyl group, 1,3-diacylguanidino-lower ($C_{1-4}$) alkyl-phenyl group, phenyl group substituted by halogen and lower ($C_{1-4}$)alkyl, phenyl group substituted by halogen and lower ($C_{1-4}$)alkoxy-carbonyl, phenyl group substituted by halogen and cyano, phenyl group substituted by halogen and 5-membered aromatic heterocyclic group, phenyl group substituted by halogen and lower ($C_{1-4}$)alkoxy-carbonyl-lower ($C_{1-4}$)alkyl-carbamoyl and the like are used.

As the halogeno phenyl group, for example, 2,3-difluorophenyl group, 2,3-dichlorophenyl group, 2,4-difluorophenyl group, 2,4-dichlorophenyl group, 2,5-difluorophenyl group, 2,5-dichlorophenyl group, 2,6-difluorophenyl group, 2,6-dichlorophenyl group, 3,4-difluorophenyl group, 3,4-dichlorophenyl group, 3,5-difluorophenyl group, 3,5-dichlorophenyl group, 2-fluorophenyl group, 2-chlorophenyl group, 3-fluorophenyl group, 3-chlorophenyl group, 4-fluorophenyl group, 4-chlorophenyl group, 2-fluoro-4-chlorophenyl group, 2-chloro-4-fluorophenyl group, 4-bromo-2-fluorophenyl group, 2,3,4-trifluorophenyl group, 2,4,5-trifluorophenyl group, 2,4,6-trifluorophenyl group and the like are used.

As the lower ($C_{1-4}$)alkyl-phenyl group, for example, 2-ethylphenyl group, 2,6-diisopropylphenyl group and the like are preferably used, and as the lower ($C_{1-4}$)alkoxy-phenyl group, for example, 4-methoxyphenyl and the like are preferably used.

As the lower ($C_{1-4}$)alkoxy-carbonylphenyl group, for example, 2-ethoxycarbonylphenyl group, 2-methoxycarbonylphenyl group, 4-methoxycarbonylphenyl group and the like are preferably used; as the halogeno lower ($C_{1-4}$)alkylphenyl group, for example, 2-trifluoromethylphenyl group and the like are preferably used; and as the halogeno lower ($C_{1-4}$) alkoxy-phenyl group, for example, 2-trifluoromethoxyphenyl group, 4-(2,2,3,3,3-pentafluoropropoxy)phenyl group and the like are preferably used.

As the lower ($C_{1-4}$)alkanoyl-phenyl group, for example, 2-acetylphenyl group and the like are preferably used; as the phenyl group substituted by 5-membered aromatic heterocyclic group, for example, 4-(2H-1,2,3-triazol-2-yl)phenyl group, 4-(2H-tetrazol-2-yl)phenyl group, 4-(1H-tetrazol-1-yl)phenyl group, 4-(1H-1,2,3-triazol-1-yl)phenyl group and the like are preferably used; as the lower ($C_{1-4}$)alkoxy-carbonyl-lower ($C_{1-4}$)alkyl-carbamoylphenyl group, for example, 4-(N-ethoxycarbonylmethylcarbamoyl)phenyl group and the like are preferably used; and as the 1,3-diacylguanidino-lower ($C_{1-4}$)alkyl-phenyl group, for example, 4-(1,3-bis-tert-butoxycarbonylguanidinomethyl)phenyl group and the like are preferably used.

As the phenyl group substituted by halogen and lower ($C_{1-4}$)alkyl group, for example, 2-fluoro-4-methylphenyl group, 2-chloro-4-methylphenyl group, 4-fluoro-2-methylphenyl group and the like are preferably used; as the phenyl group substituted by halogen and lower ($C_{1-4}$)alkoxy-carbonyl, for example, 2-chloro-4-methoxycarbonylphenyl group and the like are preferably used; as the phenyl group substituted by halogen and cyano, 2-chloro-4-cyanophenyl group and the like are preferably used; as the phenyl group substituted by halogen and 5-membered aromatic heterocyclic group, for example, 2-fluoro-4-(1H-1,2,4-triazol-1-yl)phenyl and the like are preferably used; and as the phenyl group substituted by halogen and lower ($C_{1-4}$)alkoxy-carbonyl-lower ($C_{1-4}$)-alkyl-carbamoyl, for example, 2-chloro-4-(N-tert-butoxycarbonylmethylcarbamoyl)phenyl group, 2-chloro-4-(N-ethoxycarbonylmethylcarbamoyl)phenyl group and the like are preferably used.

As Ar, halogeno phenyl group, phenyl group substituted by lower ($C_{1-4}$)alkyl-phenyl group, halogen and lower ($C_{1-4}$) alkoxy-carbonyl and the like are preferably used.

More specifically, as Ar, phenyl group, phenyl group substituted by 1 to 3 (particularly 1 or 2) halogen (e.g., 2,3-difluorophenyl group, 2,3-dichlorophenyl group, 2,4-difluorophenyl group, 2,4-dichlorophenyl group, 2,5-difluorophenyl group, 2,5-dichlorophenyl group, 2,6-difluorophenyl group, 2,6-dichlorophenyl group, 3,4-difluorophenyl group, 3,4-dichlorophenyl group, 3,5-difluorophenyl group, 3,5-dichlorophenyl group, 4-bromo-2-fluorophenyl group, 2-fluorophenyl group, 2-chlorophenyl group, 3-fluorophenyl group, 3-chlorophenyl group, 4-fluorophenyl group, 4-chlorophenyl group, 2-fluoro-4-chlorophenyl group, 2-chloro-4-fluorophenyl group, 2,3,4-trifluorophenyl group, 2,4,5-trifluorophenyl group and the like), phenyl group substituted by halogen and lower ($C_{1-4}$)alkyl (e.g., 2-chloro-4-methylphenyl group, 4-fluoro-2-methylphenyl group and the like) and the like are preferable. Of these, phenyl group substituted by 1 to 3 (particularly 1 or 2) halogen (e.g., 2,3-dichlorophenyl group, 2,4-difluorophenyl group, 2,4-dichlorophenyl group, 2,6-dichlorophenyl group, 2-fluorophenyl group, 2-chlorophenyl group, 3-chlorophenyl group, 2-chloro-4-fluorophenyl group, 2,4,5-trifluorophenyl group and the like), phenyl group substituted by halogen and lower ($C_{1-4}$)alkyl (e.g., 2-chloro-4-methylphenyl group, 4-fluoro-2-methylphenyl group and the like) and the like are preferable. Particularly, as Ar, a group represented by the formula (c) is preferable and a group represented by the formula (c1) is more preferable. As the halogen atom which is a substituent represented by $R^3$ in the formula (c) and ring B, and halogen atom represented by $R^{3a}$ and $R^{3b}$ in the formula (c1), fluorine atom and chlorine atom are preferable. As the lower alkyl group represented by $R^3$ in the formula (c), $C_{1-4}$ alkyl group such as methyl, ethyl, propyl and the like are used. Of the groups represented by the formula (c), 2,4-difluorophenyl group, 2-chloro-4-fluorophenyl group, 2-methyl-4-chlorophenyl group and the like are preferable. Of the groups represented by the formula (c1), 2,4-difluorophenyl group, 2-chloro-4-fluorophenyl group and the like are preferable.

X shows methylene group, nitrogen atom, sulfur atom or oxygen atom. Of these, nitrogen atom, sulfur atom and oxygen atom are preferable.

The ring A is a 5 to 8-membered ring substituted by a group of the formula: —CO—$R^1$ wherein $R^1$ is as defined above and a group of the formula: —$SO_2$—Y—Ar wherein Y and Ar are as defined above, which is optionally substituted by 1 to 4 substituent(s) selected from (i) aliphatic hydrocarbon group optionally having substituent(s), (ii) aromatic hydrocarbon group optionally having substituent(s), (iii) a group of the formula: OR² wherein R² is as defined above and (iv) halogen atom. It is preferably a 5 to 8-membered ring optionally substituted by 1 to 4 substituent(s) selected from (i) aliphatic hydrocarbon group optionally having substituent(s), (ii) aromatic hydrocarbon group optionally having substituent(s) and (iv) halogen atom.

These substituents may be substituted at substitutable positions on ring A. When X constituting the ring is nitrogen atom or methylene, the nitrogen atom or methylene may be substituted. When ring A is substituted by plural substituents, these substituents may be of the same kind or otherwise. It is also possible that two substituents be substituted at the same carbon atom.

As the "aliphatic hydrocarbon group optionally having substituent(s)" and "aromatic hydrocarbon group optionally having substituent(s)", which are substituents of ring A, for example, those mentioned with regard to the aforementioned "aliphatic hydrocarbon group optionally having substituent(s)" and "aromatic hydrocarbon group optionally having substituent(s)" represented by $R^1$ can be used.

As the substituent of ring A, 1 or 2 $C_{1-6}$ alkyl group(s) (e.g., $C_{1-4}$ alkyl group such as methyl group, tert-butyl group and the like), phenyl group, halogen atom (e.g., fluorine, chlorine, bromine, iodine and the like) and the like are preferably used.

The m is an integer of 0 to 2, n is an integer of 1 to 3, and the sum of m and n is not more than 4, where m is preferably 1 and n is preferably 1.

As the "lower alkyl group" of the "optionally substituted lower alkyl group" represented by $R^4$, for example, $C_{1-6}$ alkyl group such as methyl group, ethyl group, n-propyl group, isopropyl group, n-butyl group, isobutyl group and the like are mentioned, and as the "substituent", for example, hydroxyl group, $C_{1-4}$ alkoxy-carbonyl (e.g., methoxycarbonyl, ethoxycarbonyl, tert-butoxycarbonyl and the like) and the like are mentioned.

As the $R^4$, hydrogen atom and methyl group are preferable from among those mentioned above, and hydrogen atom is particularly preferable.

As the leaving group represented by $Z^1$, for example, halogen atom (e.g., chlorine, bromine, iodine and the like) and the like are preferable, and chlorine atom is particularly preferable.

The leaving group represented by $Z^2$ includes, for example, (1) a group of the formula: —SO₂N(R²)—Ar wherein R² and Ar are as defined above, (2) halogen atom, such as chlorine, bromine, iodine, fluorine and the like, (3) $C_{1-6}$ alkylsulfonyloxy group optionally substituted by 1 to 4 halogen atom(s), such as methanesulfonyloxy, ethanesulfonyloxy, butanesulfonyloxy, trifluoromethanesulfonyloxy and the like, (4) $C_{6-10}$ arylsulfonyloxy group optionally substituted by 1 to 4 halogen atom(s), such as benzenesulfonyloxy, p-toluenesulfonyloxy, p-bromobenzenesulfonyloxy, mesitylenesulfonyloxy and the like, (5) $C_{1-6}$ acylsulfonyloxy group optionally substituted by 1 to 3 halogen atom(s), such as acetyloxy, propionyloxy, trifluoroacetyloxy and the like, (6) $C_{6-10}$ arylcarbonylcarbonyloxy group, such as benzoylcarbonyloxy, phenylcarbonylcarbonyloxy and the like, and the like.

As the compound represented by the formula (I), for example, the following compound and the like are preferable.

(1) A compound (I) wherein $R^1$ is a group of the formula: $OR^{1a'}$ ($R^{1a'}$ is $C_{1-6}$ alkyl group), a group of the formula:

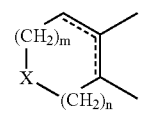

is a group of the formula:

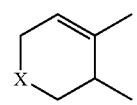

X is methylene or an oxygen atom, Y is methylene or —NH—, and Ar is phenyl group optionally substituted by 1 or 2 substituent(s) selected from the group consisting of halogen atom and $C_{1-6}$ alkoxy.

(2) A compound (I) wherein $R^1$ is a group of the formula: $OR^{1a'}$, ($R^{1a'}$ is $C_{1-6}$ alkyl group), a group of the formula:

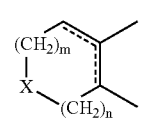

is a group of the formula:

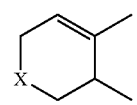

X is methylene and Y is methylene, or X is an oxygen atom and Y is —NH—, and Ar is a phenyl group optionally having two halogen atoms (e.g., 2-chloro-4-fluorophenyl group and the like).

(3) Ethyl 6-(benzylsulfonyl)-1-cyclohexene-1-carboxylate (compound 1), ethyl 6-[(4-methoxybenzyl)sulfonyl]-1-cyclohexene-1-carboxylate (compound 2), ethyl 6-[(2,4-difluorobenzyl)sulfonyl]-1-cyclohexene-1-carboxylate (compound 3), ethyl 6-[(2-chloro-4-fluorobenzyl)sulfonyl]-1-cyclohexene-1-carboxylate (compound 4), ethyl (−)-6-[(2-chloro-4-fluorobenzyl)sulfonyl]-1-cyclohexene-1-carboxylate (compound 5), ethyl (+)-6-[(2-chloro-4-fluorobenzyl)sulfonyl]-1-cyclohexene-1-carboxylate (compound 6), ethyl 3-[(2,4-difluorophenyl)sulfamoyl]-3,6-dihydro-2H-pyran-4-carboxylate (compound 7) or ethyl 3-[(2-chloro-4-fluorophenyl)sulfamoyl]-3,6-dihydro-2H-pyran-4-carboxylate (compound 8).

(4) Ethyl 6-[(2-chloro-4-fluorobenzyl)sulfonyl]-1-cyclohexene-1-carboxylate (compound 4), ethyl (+)-6-[(2-chloro-4-fluorobenzyl)sulfonyl]-1-cyclohexene-1-carboxylate (compound 6) or ethyl 3-[(2-chloro-4-fluorophenyl)sulfamoyl]-3,6-dihydro-2H-pyran-4-carboxylate (compound 8).

The salt of the compound of the formula (I) is exemplified by a salt with inorganic base, a salt with organic base, a salt with inorganic acid, a salt with organic acid, and a salt with basic or acidic amino acid. Examples of the salt with inorganic base include alkali metal salts such as sodium salt, potassium salt and the like, alkaline earth metal salts such as calcium salt, magnesium salt and the like, aluminum salt and ammonium salt, examples of the salt with organic base include salts with trimethylamine, triethylamine, pyridine, picoline, ethanolamine, diethanolamine, triethanolamine, dicyclohexylamine, N,N'-dibenzylethylenediamine and the like, examples of the salt with inorganic acid include salts with hydrochloric acid, hydrobromic acid, nitric acid, sulfuric acid, phosphoric acid and the like, examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like, examples of the salt with basic amino acid include salts with arginine, lysine, ornithine and the like, and examples of the salt with acidic amino acid include salts with aspartic acid, glutamic acid and the like.

When the compound of the formula (I) or a salt thereof has a stereoisomer, each stereoisomer thereof and a mixture of the stereoisomers are encompassed in the present invention.

While the compound of the formula (I) and a salt thereof have an enantiomer, each enantiomer thereof and a mixture of the enantiomers are encompassed in the present invention.

The production method of compound (I) of the formula (I) and a salt thereof [hereinafter sometimes to be referred to as compound (I)] is explained in the following.

A compound of the formula (I) wherein X is nitrogen atom, sulfur atom or oxygen atom and Y is an optionally substituted nitrogen atom, or a salt thereof, namely, a compound of the formula (Ia) and a salt thereof [hereinafter sometimes to be referred to as compound (Ia)] can be produced by, for example, reacting a compound of the formula (II) or a salt thereof [hereinafter sometimes to be referred to as compound (II)] and a compound of the formula (III) or a salt thereof [hereinafter sometimes to be referred to as compound (III)], and where necessary, hydrolyzing the resulting product by a method known per se. The salt of a compound of the formula (II) and the salt of a compound of the formula (III) are exemplified by those similar to the salts mentioned with regard to the aforementioned compound of the formula (I).

The reaction between compound (II) and compound (III) can be carried out without solvent but it is generally carried out in a solvent inert to the reaction. The solvent includes, for example, sulfoxides (e.g., dimethyl sulfoxide etc.), ethers (e.g., diethyl ether, tetrahydrofuran, dioxane etc.), nitrites (e.g., acetonitrile etc.), aromatic hydrocarbons (e.g., benzene, toluene, xylene etc.), halogenated hydrocarbons (e.g., dichloromethane, chloroform, 1,2-dichloroethane etc.), esters (e.g., ethyl acetate etc.), amides (e.g., dimethylformamide, acetamide, dimethylacetamide, 1,3-dimethyl-2-imidazolidinone, 1-methyl-2-pyrrolidone etc.) and the like. Only one kind of these solvents may be used, or two or more kinds thereof may be mixed at a suitable ratio and used. While the amount of the solvent to be used is not particularly limited, generally, it is preferably 2-300 times the weight of compound (II). This reaction is preferably carried out in the presence of a base, and as the base, an inorganic base (e.g., sodium hydride, potassium hydride, sodium hydroxide etc.), and an organic base (e.g., triethylamine, pyridine, diisopropylethylamine, DBU etc.) can be used. Particularly, an organic base such as triethylamine is preferably used. When a base is used, the amount thereof is preferably about 0.5 to about 5-fold amount (molar ratio), more preferably about 0.9 to about 2-fold amount (molar ratio), relative to compound (II). The amount of use of compound (III) is preferably about 1 to about 5-fold amount (molar ratio), more preferably about 1 to about 2-fold amount (molar ratio), based on compound (II). The reaction temperature is preferably about −10 to about 100° C., more preferably about 0 to about 60° C. The reaction time is preferably about 0.5 to about 50 hours, more preferably about 0.5 to about 30 hours.

During the course of reaction between compound (II) and compound (III), compound (Ia) may be synthesized due to isomerization of a group of the formula (b2) of compound (II) to a group of the formula (b1).

In this reaction, when a compound of the formula (Ia) wherein $R^1$ is $OR^{1a}$, where $R^{1a}$ is an optionally substituted aliphatic hydrocarbon, is obtained, this compound is hydrolyzed to give a compound of the formula (Ia) wherein $R^1$ is OH. The hydrolysis can be performed according to a method known per se.

When compound (Ia) thus obtained has a free acidic group or basic group, it can be converted, where necessary, to a salt by a conventional method.

A compound of the formula (I) wherein Y is optionally substituted methylene group and a salt thereof can be produced by, for example, reacting a compound of the formula (IV) or a salt thereof [hereinafter sometimes to be also referred to as compound (IV)] and a compound of the formula (V1) or a salt thereof [hereinafter sometimes to be also referred to as compound (V1)], oxidizing the resulting sulfide with an oxidizing agent, and, where necessary, subjecting the product to hydrolysis. The salt of a compound of the formula (IV) and the salt of a compound of the formula (V1) are exemplified by those similar to the salts mentioned with regard to the aforementioned compound of the formula (I).

The reaction between compound (IV) and compound (V1) can be carried out without solvent or in a solvent that does not inhibit the reaction. The solvent includes, for example, sulfoxides (e.g., dimethyl sulfoxide etc.), ethers (e.g., diethyl ether, tetrahydrofuran, dioxane etc.), nitrites (e.g., acetonitrile etc.), aromatic hydrocarbons (e.g., benzene, toluene, xylene etc.), halogenated hydrocarbons (e.g., dichloromethane, chloroform, 1,2-dichloroethane etc.), esters (e.g., ethyl acetate etc.), amides (e.g., dimethylformamide, acetamide, dimethylacetamide, 1,3-dimethyl-2-imidazolidinone, 1-methyl-2-pyrrolidone etc.) and the like. Only one kind of these solvents may be used, or two or more kinds thereof may be mixed at a suitable ratio and used. While the amount of the solvent to be used is not particularly limited, generally, it is preferably 2-300 times the weight of compound (IV).

This reaction is preferably carried out in the presence of a base, and as the base, an inorganic base (e.g., potassium carbonate, sodium hydride, potassium hydride, sodium hydroxide etc.) or an organic base (e.g., triethylamine, pyridine, diisopropylethylamine, DBU, potassium t-butoxide etc.) is preferably used. The amount of use when a base is present is preferably about 0.5 to about 5-fold amount (molar ratio), more preferably about 0.9 to about 2-fold amount (molar ratio), relative to compound (VI). The amount of use of the compound (V1) is preferably about 1 to about 5-fold amount (molar ratio), more preferably about 1 to about 2-fold amount (molar ratio), based on compound (IV). The reaction temperature is preferably from about −10 to about 100° C., more preferably from about 0 to about 60° C. The reaction time is preferably from about 0.1 to about 50 hours, more preferably from about 0.5 to about 10 hours.

As a result of the above-mentioned reaction, sulfide is produced. The reaction to oxidize this sulfide is generally carried out in a solvent that does not inhibit the reaction. As the solvent, aromatic hydrocarbons (e.g., benzene, toluene, xylene etc.), halogenated hydrocarbons (e.g., dichloromethane, chloroform, 1,2-dichloroethane etc.), esters (e.g., ethyl acetate etc.) and the like are used. Only one kind of these solvents may be used, or two or more kinds thereof may be mixed at a suitable ratio and used. Examples of the oxidizing agent include oxygen-light, hydrogen peroxide, perbenzoic acids such as perbenzoic acid, m-chloroperbenzoic acid and the like, for example perchlorate such as lithium perchlorate, silver perchlorate, mercury(II) perchlorate, tetrabutylammonium perchlorate and the like, nitrosylsulfuric acid, alkylnitrite such as isoamyl nitrite and the like, halogen such as iodine, bromine, chlorine and the like, N-bromosuccinic imide, sulfuryl chloride, chloramine T and the like. The reaction temperature is preferably from about −30 to about 30° C., more preferably from about −10 to about 10° C. The reaction time is preferably from about 0.1 to about 50 hours, more preferably from about 0.5 to about 10 hours.

In this reaction, when a compound of the formula (Ia), wherein $R^1$ is $OR^{1a}$ and $R^{1a}$ is an optionally substituted aliphatic hydrocarbon, is obtained, this compound is hydrolyzed to give a compound of the formula (Ia) wherein $R^1$ is OH. This hydrolysis is performed by a method known per se.

When the thus-obtained compound (Ia) has a free acidic group or basic group, it can be converted to a salt as necessary by a conventional method.

The thus-obtained compound (I) of the present invention can be isolated and purified from the reaction mixture by a method known per se, such as extraction, concentration, neutralization, filtration, recrystallization, chromatography and the like.

The prodrug of the compound (I) of the present invention is a compound that is converted to compound (I) by a reaction with an enzyme, gastric acid and the like in the body under physiological conditions. In other words, it is a compound that undergoes enzymatic oxidation, reduction, hydrolysis and the like into compound (I), or a compound that undergoes hydrolysis and the like due to gastric acid and the like into compound (I). The prodrug of compound (I) is a compound (I) wherein amino group is acylated, alkylated or phosphorylated (e.g., a compound (I) wherein amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like); a compound (I) wherein hydroxyl group is acylated, alkylated, phosphorylated or borated (e.g., a compound (I) wherein hydroxyl group is acetylated, palmitoylated, propanoylated, pivaloylated, succinylated, fumarylated, alanylated, dimethylaminomethylcarbonylated and the like); a compound (I) wherein carboxyl group is esterified or amidated (e.g., a compound (I) wherein carboxyl group is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methyl amidated and the like); and the like. These compounds can be produced from compound (I) by a method known per se.

The prodrug of compound (I) may be a compound that is converted to compound (I) under the physiological conditions described in Development of Pharmaceutical Products, vol. 7, Molecule Design, pp. 163-198, Hirokawa Shoten (1990).

The prodrug of the compound (I) of the present invention can be converted to similar salts.

The compound (I) of the present invention may be a hydrate or anhydride, and the prodrug of the compound (I) of the present invention may also be a hydrate or anhydride.

The compound (I) of the present invention may be labeled with an isotope (e.g., $^3H$, $^{14}C$, $^{35}S$, $^{125}I$) and the like, and the prodrug of the compound (I) of the present invention may be also labeled.

When the compound (I) of the present invention has an asymmetric carbon in ring A, at least two stereoisomers or enantiomers can exist, which isomers can be individually produced when desired.

When the compound (I) is a mixture of two or more kinds of isomers, these can be separated into each isomer by a typical separation method, such as a method for generating a salt with an optically active acid (e.g., camphor sulfonic acid etc.) or an optically active base (e.g., 1-methylbenzylamine etc.) or a separation method using various chromatographys (e.g., liquid chromatography using an optically active column etc.), fractional recrystallization and the like.

The starting compound (II) in the present invention can be produced by, for example, a method shown by the following reaction formula:

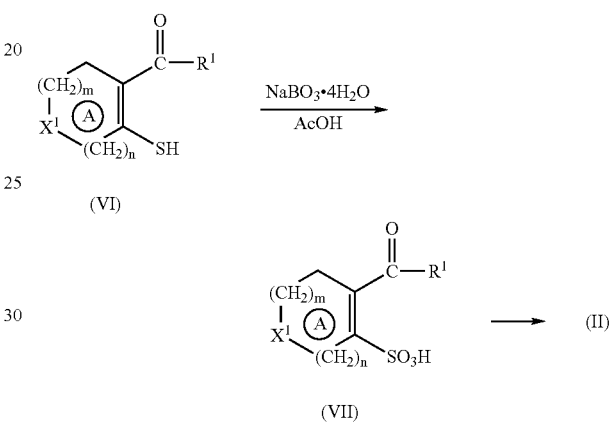

wherein each symbol is as defined above.

The compound (VI) is oxidized with sodium perborate in acetic acid to give compound (VII). The compound (VII) is reacted with thionyl halide (e.g., thionyl chloride and the like) or substituted sulfonyl chloride (e.g., methanesulfonyl chloride, benzenesulfonyl chloride and the like) to give compound (II).

The starting compound or synthetic intermediate obtained by the aforementioned method can be isolated and purified from a reaction mixture by a method known per se, such as extraction, concentration, neutralization, filtration, recrystallization, column chromatography, thin-layer chromatography and the like. It is also possible to use the reaction mixture without isolation in the next step.

In each of the above-mentioned reactions, a protecting group of amino group, carboxyl group and hydroxy group, which are not involved in the reaction, may be used for the compound or a salt thereof subjected to the reaction. The addition and removal of the protecting group can be performed according to a known method.

The protecting group of the amino group is, for example, formyl and respectively optionally substituted $C_{1-6}$ alkylcarbonyl (for example, acetyl, propionyl and the like), phenylcarbonyl, $C_{1-6}$ alkyl-oxycarbonyl (e.g., methoxycarbonyl, ethoxycarbonyl and the like), phenyloxycarbonyl, $C_{7-10}$ aralkyloxy-carbonyl (e.g., phenyl-$C_{1-4}$ alkyloxy-carbonyl such as benzyloxycarbonyl and the like, and the like), trityl, phthaloyl or N,N-dimethylaminomethylene and the like. As a substituent thereof, halogen atom (e.g., fluorine, chlorine, bromine, iodine and the like), formyl, $C_{1-6}$ alkyl-carbonyl (e.g., acetyl, propionyl, valeryl and the like), nitro group and the like are used, wherein the number of substituent is about 1 to 3.

The protecting group of carboxyl group is, for example, optionally substituted $C_{1-6}$ alkyl (e.g., methyl, ethyl, propyl, isopropyl, butyl, tert-butyl and the like), phenyl, trityl or silyl and the like. As a substituent thereof, halogen atom (e.g., fluorine, chlorine and the like), formyl, $C_{1-6}$ alkyl-carbonyl (e.g., acetyl, propionyl, valeryl and the like), nitro group and the like are used, wherein the number of substituent is about 1 to 3.

The protecting group of hydroxy group is, for example, optionally substituted $C_{1-6}$ alkyl (e.g., methyl, ethyl, propyl, isopropyl, butyl, tert-butyl and the like), phenyl, $C_{7-10}$ aralkyl (e.g., phenyl-$C_{1-4}$ alkyl such as benzyl and the like, and the like), formyl, $C_{1-6}$ alkyl-carbonyl (e.g., acetyl, propionyl and the like), phenyloxycarbonyl, benzoyl, ($C_{7-10}$ aralkyloxy)carbonyl (e.g., phenyl-$C_{1-4}$ alkyloxy-carbonyl such as benzyloxycarbonyl and the like, and the like), pyranyl, furanyl, silyl and the like. As a substituent thereof, halogen atom ((e.g., fluorine, chlorine and the like), $C_{1-6}$ alkyl (e.g., methyl, ethyl, propyl and the like), phenyl, $C_{7-10}$ aralkyl (e.g., phenyl-$C_{1-4}$ alkyl such as benzyl and the like, and the like), nitro group and the like are used, wherein the number of substituent is about 1 to 4.

The protecting group can be removed by a method known per se or a similar method. For example, a method including treating with acid, base, reduction, ultraviolet, hydrazine, phenylhydrazine, sodium N-methyldithiocarbamate, tetrabutylammonium fluoride, palladium acetate and the like is used.

The compound (I) of the present invention, a salt thereof and a prodrug thereof (hereinafter the compound (I) of the present invention) show low toxicity, and have a nitric oxide (NO) production-inhibitory activity and an inhibitory activity on the production of inflammatory cytokine such as TNF-α, IL-1, IL-6 and the like. They are useful as a drug for the treatment and/or prophylaxis of diseases such as cardiac disease, autoimmune disease, inflammatory disease, central nervous system disease, infectious disease, sepsis, septic shock and the like in mammals (e.g., cat, cattle, dog, horse, goat, monkey, human and the like), for example, ichorrhemia, endotoxin shock, exotoxin shock, heart failure, shock, hypotension, rheumatoid arthritis, arthrosteitis, gastritis, ulcerative colitis, peptic ulcer, stress gastric ulcer, Crohn's disease, autoimmune disease, tissue injury and rejection after organ transplantation, ischemic reperfusion disorder, acute coronary microvascular occlusion, shock vascular occlusion (disseminated intravascular coagulation syndrome (DIC) and the like), ischemic brain disorder, arteriosclerosis, pernicious anemia, Fanconi's anemia, sickle cell anemia, pancreatitis, nephrotic syndrome, nephritis, renal failure, insulin-dependent diabetes mellitus, non-insulin dependent diabetes mellitus, hepatic porphyria, alcoholism, Parkinson's disease, chronic leukemia, acute leukemia, tumor, myeloma, relief of side effects of anticancer agent, infant and adult respiratory distress syndrome, pulmonary emphysema, dementia, Alzheimer's disease, multiple sclerosis, vitamin E deficiency, aging, sunburn, myodystrophy, myocarditis, cardiac myopathy, myocardial infarction, sequela of myocardial infarction, osteoporosis, pneumonia, hepatitis, psoriasis, pain, cataract, influenza infection, malaria, human immunodeficiency virus (HIV) infection, radiation injury, burn, improved efficiency of in vitro fertilization, hypercalcemia, ankylosing spondylitis, osteopenia, bone Behcet's disease, osteomalacia, bone fracture, acute bacterial meningitis, *Helicobacter pylori* infection, invasive staphylococcal infection, tuberculosis, systemic mycotic infection, herpes simplex virus infection, varicella-zoster virus infection, human papilloma virus infection, acute virus encephalitis, encephalitis, asthma, atopic dermatitis, allergic rhinitis, reflux esophagitis, fever, hypercholesterolemia, hyperglyceridemia, hyperlipidemia, diabetic complications, diabetic nephropathy, diabetic neuropathy, diabetic retinopathy, gout, gastric atony, hemorrhoid, systemic lupus erythematodes, spinal trauma, agrypnia, schizophrenia, epilepsy, cirrhosis, hepatic failure, unstable angina pectoris, valvular disease of heart, thrombocytopenia derived from dialysis, acute ischemic stroke, acute brain thrombosis, cancer metastasis, bladder cancer, breast cancer, cervical cancer, colon cancer, stomach cancer, ovarian cancer, prostate cancer, small cell lung cancer, non-small cell lung cancer, malignant melanoma, Hodgkin's disease, non-Hodgkin's lymphoma and the like.

When the compound (I) of the present invention is administered to human, the compound itself or the compound after admixing with a suitable pharmacologically acceptable carrier, excipient, diluent and the like can be administered orally or parenterally as a safe pharmaceutical composition, such as an oral administration agent (e.g., powder, granule, tablet, capsule etc.), a parenteral administration agent (e.g., injection, an external preparation (e.g., nasal preparation, percutaneous preparation etc.)), a suppository (e.g., rectal suppository, vaginal suppository and the like) and the like.

These preparations can be produced by, for example, applying a method known per se generally employed for the production of pharmaceutical preparations.

The content of the compound (I) of the present invention in the preparation varies depending on the dosage form. For example, the content thereof in the aforementioned oral administration agent is about 1 to about 99 wt %, preferably about 10 to 99 wt %, more preferably about 10 to about 95 wt %. In the aforementioned parenteral administration agent, for example, it is about 0.001 to about 99 wt %, preferably about 0.001 to about 95 wt %.

The content of the components other than compound (I) in the preparation is generally about 1 to 99.999 wt %, preferably about 10 to about 90 wt %.

For injection, for example, an aqueous injection can be prepared using the compound (I) of the present invention together with a solubilizer (e.g., β-cyclodextrins etc.), a dispersing agent (e.g., Tween 80 (Atlas Powder Co., USA), HCO60 (Nikko Chemicals Co., Ltd.), carboxymethylcellulose, sodium alginate etc.), a preservative (e.g., methylparabene, propylparabene, benzyl alcohol, chlorobutanol etc.), an isotonic agent (e.g., sodium chloride, glycerine, sorbitol, glucose etc.) and the like according to a conventional method. Alternatively, an oily injection can be formed by dissolving, suspending or emulsifying as appropriate the compound in a vegetable oil (e.g., olive oil, sesame oil, peanut oil, cottonseed oil, corn oil etc.), propylene glycol and the like.

An oral administration agent can be produced by adding, for example, an excipient (e.g., lactose, sucrose, starch etc.), a disintegrant (e.g., starch, calcium carbonate etc.), a binder (e.g., starch, gum arabic, carboxymethylcellulose, polyvinylpyrrolidone, hydroxypropylcellulose etc.), a lubricant (e.g., talc, magnesium stearate, polyethylene glycol 6000 etc.) and the like as appropriate to compound (I) of the present invention, compression-shaping, and where necessary, applying a coating and the like aiming at masking of taste, enteric property or sustained release according to a method known per se. Examples of the coating agent include hydroxypropylmethylcellulose, ethylcellulose, hydroxymethylcellulose, hydroxypropylcellulose, polyoxyethylene glycol, Tween 80, pluronic F68, cellulose acetate phthalate, hydroxypropylmethyl cellulose phthalate, hydroxymethylcellulose acetate succinate, Eudragit (Rohm Pharm GmbH, Germany, a copolymer of methacrylic acid with acrylic acid), pigment (e.g., titanium oxide, bengara etc.) and the like.

The compound (I) of the present invention can be also used as a solid, semi-solid or liquid external agent.

For example, a solid external agent can be produced from the compound (I) of the present invention as it is, or by adding an excipient (e.g., glycol, mannitol, starch, crystalline cellulose etc.), a thickener (e.g., natural gums, cellulose derivative, acrylic polymer etc.) and the like, mixing the same and preparing into a powdery composition. A semi-solid external agent can be produced by a conventional method and preferably used as an aqueous or oily gel, or an ointment. A liquid external preparation can be produced by preparing into an oily or aqueous suspension according to a method employed for production of injection or a similar method.

In addition, a pH-adjusting agent (e.g., carbonic acid, phosphoric acid, citric acid, hydrochloric acid, sodium hydroxide etc.), a preservative (e.g., p-oxybenzoic acid esters, chlorobutanol, benzalkonium chloride etc.) and the like may be added as appropriate to a solid, semi-solid or liquid external agent. To be specific, for example, an ointment can be prepared, which contains the compound (I) of the present invention generally by about 0.1 to about 100 mg per 1 g, using petrolatum, lanolin and the like as a base material.

The compound (I) of the present invention can be also prepared into an oily or aqueous solid, semi-solid or liquid suppository. The oily base used as appropriate for producing suppository is, for example, higher fatty acid glyceride (e.g., cacao butter, Witepsols (Dynamitnobel Ltd.) etc.), middle fatty acid (e.g., migriol acid (Dynamitnobel Co., Ltd.) etc.), vegetable oil (e.g., sesame oil, soybean oil, cottonseed oil etc.) and the like. As an aqueous base, for example, polyethylene glycols, propylene glycol and the like are used, and as an aqueous gel base, for example, natural gums, cellulose derivative, vinyl polymer, acrylic polymer and the like are used as appropriate.

While the dose of the compound (I) of the present invention varies depending on the age, body weight, condition, dosage form, administration method, administration period and the like, for example, it is generally about 0.01 to about 1000 mg/kg, preferably about 0.01 to about 100 mg/kg, more preferably about 0.1 to about 100 mg/kg, particularly about 0.1 to about 50 mg/kg, specifically about 1.5 to about 30 mg/kg per day, as the amount of compound (I) of the present invention, for one patient (adult, body weight about 60 kg) with sepsis, which is orally or parenterally administered once to several times a day. It is needless to say that the dose varies depending on various conditions as mentioned above, and in some cases an amount smaller than the aforementioned dose is sufficient and in other cases administration beyond the above range may be necessary.

The prodrug of compound (I) can be used as a pharmaceutical composition like compound (I).

The present invention is explained in detail by the following Reference Examples, Examples, Formulation Examples and Experimental Examples. These examples do not limit the present invention.

The $^1$H-NMR spectrum was measured with Varian Gemini 200 (200 MHz) type spectrometer using tetramethylsilane as an internal standard, and all δ values are shown in ppm. The figures in parentheses for mixed solvents are mixing volume ratios of respective solvents. The room temperature is 15-25° C. and % means percent by weight, unless specifically indicated. The ratio of the solvents for silica gel chromatography shows the volume ratio of the solvents mixed.

Each symbol in Examples means the following. s: singlet, d: doublet, t: triplet, q: quartet, dd: double doublet, td: triple doublet, m: multiplet, br: broad, J: coupling constant

EXAMPLES

Reference Example 1

To a solution of ethyl 6-[N-(2,4-difluorophenyl)sulfamoyl]-1-cyclohexene-1-carboxylate (1 g, synthesized according to the method disclosed in JP-A-10-056492) and phenylmethanethiol (719 mg) in N,N-dimethylformamide (20 ml) was added dropwise under ice-cooling 1,8-diazabicyclo[5,4,0]-7-undecene (441 mg) and the mixture was stirred at room temperature for 18 h. The reaction mixture was diluted with ethyl acetate (100 ml), washed with water (70 ml×2) and saturated brine (70 ml), and dried over anhydrous sodium sulfate. The solvent was evaporated and the obtained residue was purified by flash silica gel column chromatography (eluent: toluene) to give ethyl 6-(benzylsulfanyl)-1-cyclohexene-1-carboxylate (673 mg) as a colorless oil.

$^1$H-NMR(CDCl$_3$)δ: 1.27 (3H, t, J=7.0 Hz), 1.55-2.36 (6H, m), 3.76 (1H, m), 3.86 (2H, s), 4.19 (2H, q, J=7.0 Hz), 6.95 (1H, t, J=4.0 Hz), 7.22-7.39 (5H, m).

Reference Example 2

In the same manner as in Reference Example 1, ethyl 6-[N-(2,4-difluorophenyl)sulfamoyl]-1-cyclohexene-1-carboxylate (1 g) and (4-methoxyphenyl)methanethiol (893 mg) were reacted to give ethyl 6-[(4-methoxybenzyl)-sulfanyl]-1-cyclohexene-1-carboxylate (848 mg) as a colorless oil.

$^1$H-NMR(CDCl$_3$) δ: 1.28 (3H, t, J=7.0 Hz), 1.57-2.32 (6H, m), 3.74 (1H, m), 3.80 (3H, s), 3.82 (2H, s), 4.20 (2H, q, J=7.0 Hz), 6.84 (2H, d, J=8.4 Hz), 6.94 (1H, t, J=4.0 Hz), 7.29 (2H, d, J=8.4 Hz).

Reference Example 3

In the same manner as in Reference Example 1, ethyl 6-[N-(2,4-difluorophenyl)sulfamoyl]-1-cyclohexene-1-carboxylate (455 mg) and (2,4-difluorophenyl)-methanethiol (421 mg) were reacted to give ethyl 6-[(2,4-difluorobenzyl)sulfanyl]-1-cyclohexene-1-carboxylate (185 mg) as a colorless oil.

$^1$H-NMR (CDCl$_3$) δ: 1.26 (3H, t, J=7.0 Hz), 1.60-2.40 (6H, m), 3.78 (1H, m), 3.84 (2H, s), 4.18 (2H, q, J=7.0 Hz), 6.76-6.88 (2H, m), 6.97 (1H, t, J=4.4 Hz), 7.34-7.46 (1H, m).

Reference Example 4

In the same manner as in Reference Example 1, ethyl 6-[N-(2,4-difluorophenyl)sulfamoyl]-1-cyclohexene-1-carboxylate (835 mg) and (2-chloro-4-fluorophenyl)-methanethiol (853 mg) were reacted to give ethyl 6-[(2-chloro-4-fluorobenzyl)sulfanyl]-1-cyclohexene-1-carboxylate (625 mg) as a colorless oil.

$^1$H-NMR (CDCl$_3$) δ: 1.26 (3H, t, J=7.0 Hz), 1.56-2.36 (6H, m), 3.82 (1H, m), 3.94 (2H, s), 4.19 (2H, q, J=7.0 Hz), 6.96 (1H, td, J=8.6 Hz, 2.6 Hz), 6.98 (1H, m), 7.12 (1H, dd, J=8.6 Hz, 2.6 Hz), 7.46 (1H, dd, J=8.6 Hz, 6.0 Hz).

Reference Example 5

3-Pyranone (20.0 g) was reacted in the same manner as described in Tetrahedron., vol. 19, p. 1625 (1963) to give ethyl 5-hydroxy-3,6-dihydro-2H-pyran-4-carboxylate (7.52 g) as a colorless oil.

¹H-NMR (CDCl₃) δ: 1.32 (3H, t, J=7.2 Hz), 2.31-2.38 (2H, m), 3.79 (2H, t, J=5.6 Hz), 4.14 (2H, t, J=1.8 Hz), 4.24 (2H, q, J=7.2 Hz), 11.85 (1H, s). SIMS: 172(M⁺).

Reference Example 6

Ethyl 5-hydroxy-3,6-dihydro-2H-pyran-4-carboxylate (12.9 g) was reacted in the same manner as described in Tetrahedron., vol. 30, p. 3753 (1974) to give ethyl 5-sulfanyl-3,6-dihydro-2H-pyran-4-carboxylate (12.0 g) as a pale-blue oil.

¹H-NMR (CDCl₃) δ: 1.32 (3H, t, J=7.2 Hz), 2.42-2.50 (2H, m), 3.70 (1H, s), 3.84 (2H, t, J=5.6 Hz), 4.22 (2H, t, J=2.2 Hz), 4.25 (2H, q, J=7.2 Hz). elemental analysis value: as C₈H₁₂O₃S Calculated (%): C, 51.04; H, 6.43; S, 17.03. Found (%): C, 50.99; H, 6.54; S, 16.91.

Reference Example 7

Sodium perborate tetrahydrate (24.5 g) was added to acetic acid (130 ml) and the mixture was heated to 50-55° C. Thereto was added dropwise a solution of ethyl 5-sulfanyl-3,6-dihydro-2H-pyran-4-carboxylate (10.0 g) in acetic acid (30 ml) over 2 h. The mixture was stirred at 50-55° C. for 3 h, and the reaction mixture was concentrated under reduced pressure. To the residue was added acetonitrile (230 ml) and the mixture was stirred at room temperature for 2 days, and the resultant insoluble material was removed off by filtration and washed with acetonitrile (70 ml). The filtrate and washing were combined and the mixture was concentrated under reduced pressure. The residue was dissolved in acetonitrile (160 ml) and the mixture was stirred at room temperature for 6 h. The obtained insoluble material was removed off by filtration, and the filtrate was concentrated under reduced pressure. To the residue was added diisopropyl ether (100 ml), and the precipitated insoluble material was filtered off to give 4-(ethoxycarbonyl)-5,6-dihydro-2H-pyran-3-sulfonic acid as a pale-yellow oil (27.6 g) containing an inorganic product.

¹H-NMR(DMSO-d₆) δ: 1.19 (3H, t, J=7.2 Hz), 2.17-2.21 (2H, m), 3.65 (2H, t, J=5.5 Hz), 4.04 (2H, q, J=7.2 Hz), 4.16 (2H, t, J=2.4 Hz).

Reference Example 8

4-(Ethoxycarbonyl)-5,6-dihydro-2H-pyran-3-sulfonic acid (27.5 g) was dissolved in thionyl chloride (82.6 ml) and the mixture was stirred at room temperature→85° C. for 3 h. The reaction mixture was concentrated to dryness under reduced pressure and the residue was dissolved in ethyl acetate (100 ml). The obtained solution was partitioned by adding diluted brine (120 ml). The ethyl acetate layer was washed twice with saturated brine (50 ml) and dried over anhydrous sodium sulfate. The solvent was evaporated and the obtained residue was purified by silica gel column chromatography (eluent:ethyl acetate/hexane=1/7→1/5). The objective product was concentrated under reduced pressure and the crystals produced by freezing were washed with hexane to give ethyl 5-(chlorosulfonyl)-3,6-dihydro-2H-pyran-4-carboxylate (7.81 g) as pale-yellow crystals.

¹H-NMR (CDCl₃) δ: 1.37 (3H, t, J=7.2 Hz), 2.62-2.70 (2H, m), 3.87 (2H, t, J=5.5 Hz), 4.34 (2H, q, J=7.2 Hz), 4.53 (2H, t, J=2.6 Hz). elemental analysis value: as C₈H₁₁ClO₅S Calculated (%): C, 37.73; H, 4.35. Found (%): C, 37.64; H, 4.27.

Example 1

To a solution of ethyl 6-(benzylsulfanyl)-1-cyclohexene-1-carboxylate (100 mg) obtained in Reference Example 1 in methylene chloride (3 ml) was added m-chloroperbenzoic acid (196 mg) under ice-cooling, and the mixture was stirred at room temperature for 1 h. To the reaction solution was added saturated aqueous sodium hydrogencarbonate solution (20 ml) and the mixture was extracted with ethyl acetate (20 ml·2). The ethyl acetate layer was washed with saturated aqueous sodium hydrogencarbonate solution (20 ml), water (20 ml) and saturated brine (20 ml), and dried over anhydrous sodium sulfate. The solvent was evaporated and the obtained residue was purified by flash silica gel chromatography (eluent: hexane→ethyl acetate/hexane=1/30) and crystallized from hexane to give ethyl 6-(benzylsulfonyl)-1-cyclohexene-1-carboxylate (compound 1, 106 mg) as white crystals.

¹H-NMR (CDCl₃) δ: 1.34 (3H, t, J=7.2 Hz), 1.41-2.50 (6H, m), 4.28 (2H, q, J=7.2 Hz), 4.29 (1H, d, J=13.8 Hz), 4.35 (1H, m), 4.55 (1H, d, J=13.8 Hz), 7.37-7.45 (4H, m) 7.50-7.55 (2H, m) elemental analysis value: as C₁₆H₂₀O₄S.0.5H₂O. Calculated (t): C, 60.55; H, 6.67. Found (%): C, 60.98; H, 6.32.

Example 2

In the same manner as in Example 1, ethyl 6-[(4-methoxybenzyl)sulfanyl]-1-cyclohexene-1-carboxylate (98 mg) obtained in Reference Example 2 was reacted to give ethyl 6-[(4-methoxybenzyl)sulfonyl]-1-cyclohexene-1-carboxylate (compound 2, 88 mg) as white crystals.

¹H-NMR (CDCl₃) d: 1.34 (3H, t, J=7.0 Hz), 1.42-2.50 (6H, m), 3.82 (3H, s), 4.21 (1H, d, J=13.6 Hz), 4.28 (2H, q, J=7.0 Hz), 4.31 (1H, m), 4.50 (1H, d, J=13.6 Hz), 6.92 (2H, d, J=8.8 Hz), 7.41 (1H, t, J=3.6 Hz), 7.47 (2H, d, J=8.8 Hz). Elemental analysis value: as C₁₇H₂₂O₅S Calculated (%): C, 60.33; H, 6.55. Found (%): C, 60.42; H, 6.58.

Example 3

In the same manner as in Example 1, ethyl 6-[(2,4-difluorobenzyl)sulfanyl]-1-cyclohexene-1-carboxylate (161 mg) obtained in Reference Example 3 was reacted to give ethyl 6-[(2,4-difluorobenzyl)sulfonyl]-1-cyclohexene-1-carboxylate (compound 3, 134 mg) as white crystals.

¹H-NMR (CDCl₃) δ: 1.32 (3H, t, J=7.0 Hz), 1.59-2.50 (6H, m), 4.27 (2H, q, J=7.0 Hz), 4.35 (1H, d, J=14.0 Hz), 4.39 (1H, m), 4.51 (1H, d, J=14.0 Hz), 6.83-6.96 (2H, m), 7.42 (1H, t, J=4.0 Hz), 7.49-7.61 (1H, m). Elemental analysis value: as C₁₆H₁₈F₂O₄S Calculated (%): C, 55.80; H, 5.27. Found (%): C, 55.95; H, 5.40.

Example 4

In the same manner as in Example 1, ethyl 6-[(2-chloro-4-fluorobenzyl)sulfanyl]-1-cyclohexene-1-carboxylate (509 mg) obtained in Reference Example 4 was reacted to give ethyl 6-[(2-chloro-4-fluorobenzyl)-sulfonyl]-1-cyclohexene-1-carboxylate (compound 4, 422 mg) as white crystals.

¹H-NMR (CDCl₃) δ: 1.32 (3H, t, J=7.0 Hz), 1.55-2.52 (6H, m), 4.25 (2H, q, J=7.0 Hz), 4.41 (1H, d, J=5.6 Hz), 4.59 (2H, s), 7.03 (1H, td, J=8.4 Hz, 2.6 Hz), 7.21 (1H, dd, J=8.4 Hz, 2.6 Hz), 7.42 (1H, t, J=4.0 Hz), 7.62 (1H, dd, J=8.4 Hz, 6.2 Hz). Elemental analysis value: as C₁₆H₁₈ClFO₄S Calculated (%): C, 53.26; H, 5.03. Found (%): C, 53.08; H. 4.95.

Example 5

Ethyl 6-[(2-chloro-4-fluorobenzyl)sulfonyl]-1-cyclohexene-1-carboxylate (compound 4, 100 mg) obtained in Example 4 was resolved in two enantiomer by high performance liquid chromatography (CHIRALPAK AD; eluent: hexane/ethanol 8/2). The eluants were filtered through a 0.45 μm filter, concentrated and crystallized from hexane to respectively give ethyl (−)-6-[(2-chloro-4-fluorobenzyl)sulfonyl]-1-cyclohexene-1-carboxylate (compound 5, 50 mg) and ethyl (+)-6-[(2-chloro-4-fluorobenzyl)sulfonyl]-1-cyclohexene-1-carboxylate (compound 6, 49 mg) each as white crystals.

Compound 5

$^1$H-NMR (CDCl$_3$) δ: 1.32 (3H, t, J=7.0 Hz), 1.56-2.55 (6H, m), 4.26 (2H, q, J=7.0 Hz), 4.42 (1H, d, J=5.6 Hz), 4.59 (2H, s), 7.03 (1H, td, J=8.6 Hz, 2.4 Hz), 7.21 (1H, dd, J=8.6 Hz, 2.4 Hz), 7.42 (1H, t, J=4.2 Hz), 7.61 (1H, dd, J=8.6 Hz, 6.0 Hz). Elemental analysis value: as C$_{16}$H$_{18}$ClFO$_4$S Calculated (%): C, 53.26; H, 5.03. Found (%): C, 53.24; H, 4.85. [α]$_D^{20}$ −97.0° (c=0.5, in methanol).

Compound 6

$^1$H-NMR (CDCl$_3$) δ: 1.32 (3H, t, J=7.0 Hz), 1.56-2.55 (6H, m), 4.26 (2H, q, J=7.0 Hz), 4.42 (1H, d, J=6.2 Hz), 4.59 (2H, s), 7.03 (1H, td, J=8.6 Hz, 2.4 Hz), 7.21 (1H, dd, J=8.6 Hz, 2.4 Hz), 7.42 (1H, t, J=4.4 Hz), 7.60 (1H, dd, J=8.6 Hz, 6.0 Hz). Elemental analysis value: as C$_{16}$H$_{18}$ClFO$_4$S Calculated (%): C, 53.26; H, 5.03. Found (%): C, 53.29; H, 4.82.

[α]$_D^{20}$ +95.0° (c=0.5, in methanol).

Example 6

2,4-Difluoroaniline (0.45 g) was dissolved in ethyl acetate (10 ml) and triethylamine (0.55 mg) was added to the obtained solution under ice-cooling. Then, a solution of ethyl 5-(chlorosulfonyl)-3,6-dihydro-2H-pyran-4-carboxylate (0.69 g) obtained in Reference Example 8 in ethyl acetate (4 ml) was added dropwise. The reaction mixture was stirred under a nitrogen stream at 0° C. for 30 min and at room temperature for 5.8 h. The reaction mixture was diluted with ethyl acetate and washed successively with water (50 ml), 0.5N hydrochloric acid (50 ml), water (50 ml×2) and saturated brine (50 ml). The ethyl acetate layer was dried over magnesium sulfate and the solvent was evaporated under reduced pressure. The residue was purified by silica gel column chromatography (eluent: ethyl acetate/hexane=1/2). The objective fraction was concentrated under reduced pressure and the residue was crystallized from a mixture of ethyl acetate and diisopropyl ether to give ethyl 3-[(2,4-difluorophenyl)-sulfamoyl]-3,6-dihydro-2H-pyran-4-carboxylate (compound 7; 0.57 g) as white crystals.

$^1$H-NMR(DMSO-d$_6$) δ: 1.14 (3H, t, J=7.0 Hz), 3.69 (1H, dd, J=12.8 Hz, 3.0 Hz), 4.08 (2H, q, J=7.0 Hz), 4.25 (2H, s), 4.33 (1H, d, J=1.8 Hz), 4.41-4.48 (1H, m), 7.00-7.05 (1H, m), 7.12 (1H, br), 7.22-7.33 (1H, m), 7.43-7.55 (1H, m), 9.82(1H, s). Elemental analysis value: as C$_{14}$H$_{15}$F$_2$NO$_5$S Calculated (%): C, 48.41; H, 4.35; N, 4.03. Found (%): C, 48.47; H, 4.35; N, 3.96.

Example 7

In the same manner as in Example 6, ethyl 5-(chlorosulfonyl)-3,6-dihydro-2H-pyran-4-carboxylate (0.70 g) obtained in Reference Example 8 was reacted with 2-chloro-4-fluoroaniline (0.52 g) to give ethyl 3-[(2-chloro-4-fluorophenyl)sulfamoyl]-3,6-dihydro-2H-pyran-4-carboxylate (compound 8; 0.54 g) as white crystals.

$^1$H-NMR(DMSO-d$_6$) δ: 1.11 (3H, t, J=7.0 Hz), 3.72 (1H, dd, J=12.8 Hz, 3.0 Hz), 4.07 (2H, q, J=7.0 Hz), 4.15-4.25 (2H, m), 4.37 (1H, d, J=2.2 Hz), 4.46-4.55 (1H, m), 7.15 (1H, br), 7.22-7.26 (1H, m), 7.46-7.59 (2H, m), 9.68(1H, s). Elemental analysis value: as C$_{14}$H$_{15}$ClFNO$_5$S Calculated (%): C, 46.22; H, 4.16; N, 3.85. Found (%): C, 46.35; H, 4.11; N, 3.73.

Specific examples of the compound of the present invention that can be synthesized in the same manner as in the aforementioned Examples are shown in Table 1 and Table 2. The present invention is not limited to the compounds exemplarily shown in Table 1 and Table 2.

TABLE 1

| Compound No. | Ar |
|---|---|
| 1 | phenyl |
| 2 | 4-OMe-phenyl |
| 3 | 3,4-difluorophenyl |
| 4 | 3-chloro-4-fluorophenyl |
| 5 (−)-form | 3-chloro-4-fluorophenyl |
| 6 (+)-form | 3-chloro-4-fluorophenyl |

General structure: cyclohexene with C(=O)OEt and SO$_2$—CH$_2$—Ar substituents.

TABLE 2

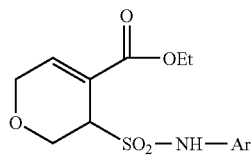

| Compound No. | Ar |
|---|---|
| 7 | 2,4-difluorophenyl (3,4-F,F) |
| 8 | 3-chloro-4-fluorophenyl |

Formulation Example 1

| | |
|---|---|
| (1) Compound 6 | 10 mg |
| (2) lactose | 60 mg |
| (3) cornstarch | 35 mg |
| (4) gelatin | 3 mg |
| (5) magnesium stearate | 2 mg |

A mixture of compound 6 (10 mg), lactose (60 mg) and cornstarch (35 mg) was granulated using a 10% aqueous gelatin solution (0.03 ml, 3 mg of gelatin) by passing through a 1 mm mesh sieve, which granules were dried at 40° C. and passed through the sieve again. The thus-obtained granules were mixed with magnesium stearate (2 mg) and compressed. The obtained core tablet was coated with a sugar coating containing an aqueous suspension of sucrose, titanium dioxide, talc and gum arabic. The coated tablets were polished with beeswax to give coated tablets.

Formulation Example 2

| | |
|---|---|
| (1) Compound 6 | 10 mg |
| (2) lactose | 70 mg |
| (3) cornstarch | 50 mg |
| (4) soluble starch | 7 mg |
| (5) magnesium stearate | 3 mg |

Compound 6 (10 mg) and magnesium stearate (3 mg) were granulated using an aqueous soluble starch solution (0.07 ml, 7 mg of soluble starch), dried and mixed with lactose (70 mg) and cornstarch (50 mg). The mixture was compressed to give tablets.

Formulation Example 3

| | |
|---|---|
| (1) Compound 8 | 10 mg |
| (2) lactose | 60 mg |
| (3) cornstarch | 35 mg |
| (4) gelatin | 3 mg |
| (5) magnesium stearate | 2 mg |

A mixture of compound 8 (10 mg), lactose (60 mg) and cornstarch (35 mg) was granulated using a 10% aqueous gelatin solution (0.03 ml, 3 mg of gelatin) by passing through a 1 mm mesh sieve, which granules were dried at 40° C. and passed through the sieve again. The thus-obtained granules were mixed with magnesium stearate (2 mg) and compressed. The obtained core tablet was coated with a sugar coating containing an aqueous suspension of sucrose, titanium dioxide, talc and gum arabic. The coated tablets were polished with beeswax to give coated tablets.

Formulation Example 4

| | |
|---|---|
| (1) Compound 8 | 10 mg |
| (2) lactose | 70 mg |
| (3) cornstarch | 50 mg |
| (4) soluble starch | 7 mg |
| (5) magnesium stearate | 3 mg |

Compound 8 (10 mg) and magnesium stearate (3 mg) were granulated using an aqueous soluble starch solution (0.07 ml, 7 mg of soluble starch), dried and mixed with lactose (70 mg) and cornstarch (50 mg). The mixture was compressed to give tablets.

Experimental Example 1

Inhibitory Activity on NO Production

Using mouse macrophage cell line, RAW264.7 as iNOS inducible cells, percent inhibition of NO production by the test compound was measured. The test compound was dissolved in N,N-dimethylformamide to 10 mM and diluted with RPMI-1640 medium to 0.1 mM. Furthermore, it was prepared with a medium to make a final concentration from 10 μM to 10 nM by diluting 10-fold, and added to the culture. The day before the experiment, the cells were prepared with RPMI-1640 medium supplemented with heat-inactivated 10% fetal calf serum to a concentration of $5 \times 10^5$ cells/ml and plated to a 96-well plate by $1 \times 10^5$ cells/0.2 ml per well. After culturing at 37° C. under 5% $CO_2$/95% air overnight, the medium was changed to RPMI-1640 medium supplemented with heat-inactivated 1% fetal calf serum. Thereto was added the prepared test compound, and LPS and interferon-γ were added to a final concentrations of 5 ng/ml and 1 U/ml, respectively. After incubation overnight, the concentration of nitrite ion (stable metabolite of NO) in the culture supernatant was measured and used as an index of NO production. The nitrite concentration was quantitatively measured by adding 20 μg/ml 2,3-diaminonaphtalene (DAN) by 25 μl to the culture supernatant (50 μl), incubating at room temperature for 10 min, adding 0.5N NaOH (25 μl) and measuring the fluorescence at 450 nm (excitation wavelength 365 nm). The results are shown in Table 3, wherein $IC_{50}$ shows the concentration of the test compound necessary for inhibiting NO production by 50%.

TABLE 3

| Compound No. | $IC_{50}$ (μM) |
| --- | --- |
| 1 | 0.24 |
| 2 | 3.2 |
| 3 | 0.047 |
| 4 | 0.029 |
| 5 | 1.0 |
| 6 | 0.0093 |
| 7 | 0.018 |
| 8 | 0.0031 |

The test compound strongly inhibited NO production by RAW264.7 cells, which shows that the cycloalkene derivative of the present invention has a superior NO production inhibitory activity.

Experimental Example 2

Inhibitory Activity on Cytokine Production

Using human monocyte cell line P31/FUJ (JCRB0091, establisher: Fujioka, obtained from the Human Science Research Resource Bank), the percent inhibition of cytokine production by the test compound was measured. The test compound was dissolved in N,N-dimethylformamide to 10 mM and diluted with RPMI-1640 medium to 0.1 mM. Furthermore, it was prepared with a medium to make a final concentration from 10 μM to 10 nM by diluting 10-fold, and added to the culture. The day before the experiment, the cells were prepared with RPMI-1640 medium supplemented with 10% fetal calf serum to a concentration of $2 \times 10^6$ cells/ml and plated to a 96-well plate by $2 \times 10^5$ cells/0.1 ml per well. The above-mentioned medium (0.1 ml) supplemented with 40 nM phorbol 12-myristate 13-acetate (PMA) was added and the mixture was cultured at 37° C. under 5% $CO_2$/95% air overnight. The cells were washed with the above-mentioned medium to remove PMA and the prepared test compound was added, and LPS and interferon-γ were added to a final concentrations of 100 ng/ml and 10 U/ml, respectively. After culturing overnight, the concentration of TNF-α and IL-1β in the culture supernatant was measured. For quantitative determination of each cytokine, a quantitative determination kit by Amersham was used. The results are shown in Table 4, wherein $IC_{50}$ shows the concentration of the test compound necessary for inhibiting cytokine production by 50%.

TABLE 4

| Compound No. | $IC_{50}$ (μM) | |
| --- | --- | --- |
| | TNF-α | IL-1β |
| 4 | 0.20 | 0.58 |
| 6 | 0.15 | 0.23 |
| 8 | 0.02 | 0.011 |

Experimental Example 3

Effect Against Increase in Blood Nitrogen Oxide Concentration

When a biological defense response against infection and the like, immunopathy and the like causes NO production in the body, it is quickly metabolized into nitrous acid and nitric acid, whereby blood nitrogen oxide concentration (NOx) increases. Using test animals, the effect of the test compound against increase in blood NOx concentration was examined.

Female BALB/c mice (7-week-old) were divided into 6-8 mice per group. For the test compound group, the test compound was suspended in 0.5% aqueous methylcellulose solution and 10 mg/kg thereof was orally administered. For the control group, a solvent was similarly administered. One hour later, LPS (10 mg/kg) was intraperitoneally administered to the test compound group and the control group. At 6 h after LPS administration, blood was drawn and nitrate ion+nitrite ion concentration in sera was measured. The nitrate ion was converted to nitrous acid ion with nitrate reductase and quantitatively measured as a total nitrite ion concentration by fluorescence method using the aforementioned DAN. The percent inhibition of the test compound group relative to the control group is shown in Table 5.

TABLE 5

| Compound No. | Blood $NO_x$ inhibition (%) |
| --- | --- |
| 4 | 62 |
| 8 | 80 |

INDUSTRIAL APPLICABILITY

The compound (I) of the present invention has an inhibitory activity on nitric oxide (NO) production and cytokine production, and is useful as an agent for the prophylaxis and/or treatment of diseases such as cardiac disease, autoimmune disease, inflammatory disease, central nervous system disease, infectious disease, sepsis, septic shock and the like.

The invention claimed is:
1. A compound of the formula:

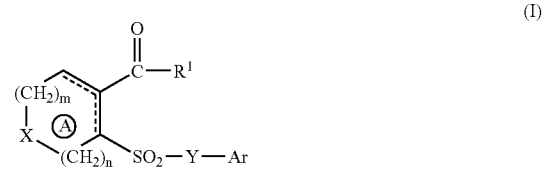

(I)

wherein
$R^1$ is a group of the formula: $OR^{1a}$ wherein $R^{1a}$ is a $C_{1-6}$ alkyl group;
X is a methylene group, —NH—, a sulfur atom or an oxygen atom;
Y is a methylene group or —NH—, each of which optionally has $C_{1-6}$ alkyl group(s); and
ring A is a 6-membered ring optionally substituted further by 1 to 4 substituent(s) selected from a $C_{1-6}$ alkyl group, a phenyl group and a halogen atom;
Ar is a $C_{6-14}$ aryl group optionally having substituent(s) selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxy group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group;

or a salt thereof and;

with the proviso that the group of the formula:

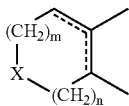 (b)

is a group of the formula:

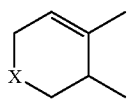

and further provided that when X is a methylene group, Y is a methylene group optionally substituted with $C_{1-6}$ alkyl group(s).

2. The compound of claim 1, wherein the ring A is a 6-membered ring optionally substituted by $C_{1-6}$ alkyl, phenyl or halogen, $R^1$ is $OR^{1a}$ where $R^{1a}$ is $C_{1-6}$ alkyl group, and Ar is a phenyl group optionally having substituent(s) selected from the group consisting of halogen atom, $C_{1-4}$ alkyl group, $C_{1-4}$ alkoxy group, $C_{1-4}$ alkoxy-carbonyl group, carboxyl group, carboxyl group, nitro group, cyano group, hydroxy group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group.

3. The compound of claim 2, wherein $R^{1a}$ is an ethyl group.

4. The compound of claim 2, wherein Ar is a halogeno phenyl group, a $C_{1-4}$ alkylphenyl group or a phenyl group substituted by halogen and $C_{1-4}$ alkyl.

5. The compound of claim 2, wherein Ar is a group of the formula:

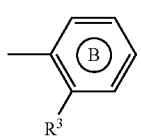 (c)

wherein $R^3$ is a halogen atom or a $C_{1-4}$ alkyl group and ring B is optionally further substituted by halogen atom.

6. The compound of claim 5, wherein Ar is a group of the formula:

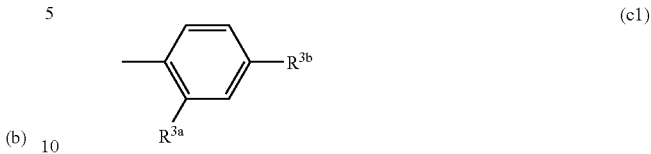 (c1)

wherein $R^{3a}$ and $R^{3b}$ are the same or different and each is a halogen atom.

7. The compound of claim 1, wherein $R^1$ is a group of the formula: $OR^{1a'}$ wherein $R^{1a'}$ is a $C_{1-6}$ alkyl group;

the group of the formula:

 (b)

is a group of the formula:

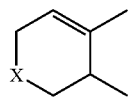

X is methylene or an oxygen atom, Y is methylene or —NH—, Ar is a phenyl group optionally having 1 or 2 substituent(s) selected from the group consisting of halogen atom and $C_{1-6}$ alkoxy.

8. The compound of claim 1, wherein $R^1$ is a group of the formula: $OR^{1a'}$ wherein $R^{1a'}$ is a $C_{1-6}$ alkyl group, the group of the formula:

 (b)

is a group of the formula:

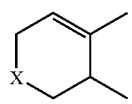

X is methylene and Y is methylene, or X is an oxygen atom and Y is —NH—, and Ar is a phenyl group optionally having two halogen atoms.

9. A method of making a compound of the formula:

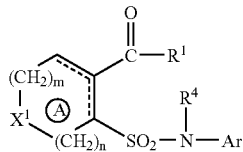
(Ia)

wherein
the group of the formula:

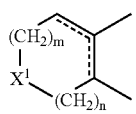
(b')

is a group of the formula:

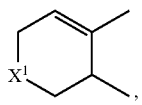

$R^1$ is a group of the formula: $OR^{1a}$ wherein $R^{1a}$ is a $C_{1-6}$ alkyl group;

$X^1$ is —NH—, a sulfur atom or an oxygen atom;

ring A is a 6-membered ring optionally substituted further by 1 to 4 substituent(s) selected from a $C_{1-6}$ alkyl group, a phenyl group and a halogen atom;

$R^4$ is a hydrogen atom or a $C_{1-6}$ alkyl group; and

Ar is a $C_{6-14}$ aryl group optionally having substituent(s) selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxy group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group;

or a salt thereof, which method comprises reacting a compound of the formula:

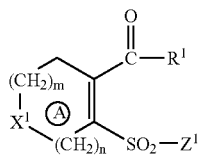
(II)

wherein $Z^1$ is a leaving group and the other symbols are as defined above, or a salt thereof and a compound of the formula:

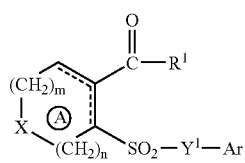
(III)

wherein each symbol is as defined above, or a salt thereof.

10. A method of making a compound of the formula:

(Ib)

wherein $R^1$ is a group of the formula: $OR^{1a}$ wherein $R^{1a}$ is a $C_{1-6}$ alkyl group;

X is a methylene group, —NH—, a sulfur atom or an oxygen atom;

ring A is a 6-membered ring optionally substituted further by 1 to 4 substituent(s) selected from a $C_{1-6}$ alkyl group, a phenyl group and a halogen atom;

$Y^1$ is a methylene group optionally having $C_{1-6}$ alkyl group(s);

Ar is a $C_{6-14}$ aryl group optionally having substituent(s) selected from the group consisting of halogen atom, $C_{1-4}$ alkyl group, $C_{1-4}$ alkoxy group, $C_{1-4}$ alkoxy-carbonyl group, carboxyl group, nitro group, cyano group, hydroxy group, $C_{1-4}$ alkanoylamino group, $C_{3-6}$ cycloalkyl group, $C_{6-10}$ aryl group, halogeno $C_{1-4}$ alkyl group, halogeno $C_{1-4}$ alkoxy group, $C_{1-4}$ alkylthio group, $C_{1-4}$ alkylsulfonyl group, $C_{1-4}$ alkanoyl group, 5-membered aromatic heterocyclic group, carbamoyl group, $C_{1-4}$ alkyl-carbamoyl group, $C_{1-4}$ alkoxy-carbonyl-$C_{1-4}$ alkyl-carbamoyl group and 1,3-diacylguanidino-$C_{1-4}$ alkyl group; and the group of the formula:

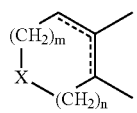
(b)

is a group of the formula:

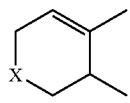

or a salt thereof, which method comprises reacting a compound of the formula:

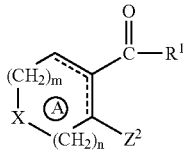
(IV)

wherein $Z^2$ is a leaving group and the other symbols are as defined above, or a salt thereof, and a compound of the formula:

HS—Y$^1$—Ar  (VI)

wherein each symbol is as defined above, or a salt thereof, and oxidizing the obtained sulfide.

11. A pharmaceutical composition comprising a compound of the formula:

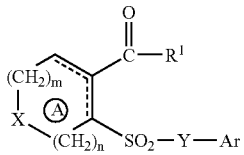
(I)

wherein
R$^1$ is a group of the formula: OR$^{1a}$ wherein R$^{1a}$ is a C$_{1-6}$ alkyl group;
X is a methylene group, —NH—, a sulfur atom or an oxygen atom;
Y is a methylene group or —NH—, each of which optionally has C$_{1-6}$ alkyl group(s); and
ring A is a 6-membered ring optionally substituted further by 1 to 4 substituent(s) selected from a C$_{1-6}$ alkyl group, a phenyl group and a halogen atom;
Ar is a C$_{6-14}$ aryl group optionally having substituent(s) selected from the group consisting of halogen atom, C$_{1-4}$ alkyl group, C$_{1-4}$ alkoxy group, C$_{1-4}$ alkoxy-carbonyl group, carboxyl group, nitro group, cyano group, hydroxy group, C$_{1-4}$ alkanoylamino group, C$_{3-6}$ cycloalkyl group, C$_{6-10}$ aryl group, halogeno C$_{1-4}$ alkyl group, halogeno C$_{1-4}$ alkoxy group, C$_{1-4}$ alkylthio group, C$_{1-4}$ alkylsulfonyl group, C$_{1-4}$ alkanoyl group, 5-membered aromatic heterocyclic group, carbamoyl group, C$_{1-4}$ alkyl-carbamoyl group, C$_{1-4}$ alkoxy-carbonyl-C$_{1-4}$ alkyl-carbamoyl group and 1,3-diacylguanidino-C$_{1-4}$ alkyl group;
a salt thereof, or a prodrug thereof in combination with a pharmaceutically acceptable carrier;
and with the proviso that the group of the formula;

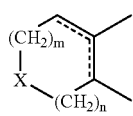
(b)

is a group of the formula:

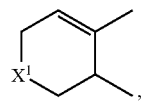

and further provided that when X is a methylene group, Y is a methylene group optionally with C$_{1-6}$ alkyl group(s).

12. A method for treating sepsis, septic shock, endotoxin shock, exotoxin shock, cytokine and/or nitric oxide-induced heart failure, shock, or cytokine and/or nitric oxide-induced hypotension, wherein said cytokine is selected from tumor necrosis factor (TNF), IL-1β, and a mixture thereof, which method comprises administering an effective amount of a compound of claim 1 or a prodrug thereof to a mammal in need thereof.

13. A method of making a pharmaceutical composition, which comprises mixing a compound of claim 1 or a prodrug thereof with a pharmacologically acceptable carrier, excipient or diluent.

14. A method for treating sepsis, septic shock, or endotoxin shock, which method comprises administering an effective amount of the compound of claim 1 or a prodrug thereof to a mammal in need thereof.

* * * * *